(12) United States Patent
Wu et al.

(10) Patent No.: US 10,853,301 B2
(45) Date of Patent: Dec. 1, 2020

(54) DATA STATISTICS FOR WEARABLE DEVICE

(71) Applicant: Anhui Huami Information Technology Co., Ltd., Anhui (CN)

(72) Inventors: Haocheng Wu, Anhui (CN); Tengrong Su, Anhui (CN)

(73) Assignee: Anhui Huami Information Technology Co., Ltd., Anhui (CN)

( * ) Notice: Subject to any disclaimer, the term of this patent is extended or adjusted under 35 U.S.C. 154(b) by 499 days.

(21) Appl. No.: 15/592,623

(22) Filed: May 11, 2017

(65) Prior Publication Data

US 2017/0249280 A1    Aug. 31, 2017

Related U.S. Application Data

(63) Continuation-in-part of application No. PCT/CN2016/088092, filed on Jul. 1, 2016.

(30) Foreign Application Priority Data

Jul. 1, 2015  (CN) .......................... 2015 1 0391594

(51) Int. Cl.
*G06F 13/42* (2006.01)
*G01C 22/00* (2006.01)
(Continued)

(52) U.S. Cl.
CPC ........ *G06F 13/4282* (2013.01); *A61B 5/0024* (2013.01); *A61B 5/024* (2013.01);
(Continued)

(58) Field of Classification Search
CPC combination set(s) only.
See application file for complete search history.

(56) References Cited

U.S. PATENT DOCUMENTS

| 10,380,321 B2 * | 8/2019 | Kamen et al. |
| 2012/0246261 A1 | 9/2012 | Roh et al. |

(Continued)

FOREIGN PATENT DOCUMENTS

| CN | 104169923 A | 11/2014 |
| CN | 104169926 A | 11/2014 |

(Continued)

*Primary Examiner* — Michael Tomaszewski
*Assistant Examiner* — William T. Monticello
(74) *Attorney, Agent, or Firm* — Young Basile Hanlon & MacFarlane, P.C.

(57) ABSTRACT

A method and an apparatus for integrating data from multiple wearable devices is provided. The method includes receiving, by a processor from a wearable device, physiological indicator data associated with a statistical item being collected for a user and a timestamp associated with the physiological indicator data, in which the statistical item is collected by the wearable device, and determining, for the user, fused physiological indicator data associated with the statistical item based on, for each of the multiple wearable devices, a priority level, the physiological indicator data, and the timestamp associated with the physiological indicator data, in which the multiple wearable devices comprise the wearable device and at least another wearable device associated with the user. The apparatus includes a processor and a memory. The memory is configured to store instructions which when executed by the processor become operational with the processor to implement the method.

17 Claims, 5 Drawing Sheets

(51) Int. Cl.
    *A61B 5/00*     (2006.01)
    *A61B 5/0205*   (2006.01)
    *G16H 40/63*    (2018.01)
    *A61B 5/024*    (2006.01)
    *A61B 5/11*     (2006.01)

(52) U.S. Cl.
    CPC .......... *A61B 5/0205* (2013.01); *A61B 5/1118* (2013.01); *G01C 22/006* (2013.01); *G16H 40/63* (2018.01); *A61B 5/681* (2013.01); *A61B 5/6803* (2013.01); *A61B 5/6807* (2013.01)

(56)           References Cited

U.S. PATENT DOCUMENTS

2014/0164611 A1     6/2014   Molettiere et al.
2015/0170531 A1*    6/2015   Hu et al.
2016/0120433 A1*    5/2016   Hughes et al.
2016/0183869 A1*    6/2016   Oh et al.
2016/0292509 A1*   10/2016   Kaps et al.
2016/0302671 A1*   10/2016   Shariff et al.

FOREIGN PATENT DOCUMENTS

CN      104219038 A    12/2014
CN      104301528 A     1/2015
CN      104537132 A     4/2015
CN      104605939 A     5/2015
CN      105593862 A     5/2016

\* cited by examiner

DATA STATISTICS FOR WEARABLE DEVICE

CROSS-REFERENCE TO RELATED APPLICATION(S)

This application is a continuation-in-part of International Application No. PCT/CN2016/088092, filed on Jul. 1, 2016, which claims priority to Chinese Patent Application No. 201510391594.8, filed on Jul. 1, 2015, the content of both of which are herein incorporated by reference in their entireties.

TECHNICAL FIELD

This disclosure relates to the field of wearable devices, and particularly relates to data statistics of the wearable devices.

BACKGROUND

Smart wearable devices are popular among consumers for their high integration of information and convenience of carrying. For example, users can use them to monitor their physiological parameters, such as walking steps, heart rates, or moving distances. In a process of monitoring human physiological parameters using the smart wearable devices, a client terminal can typically connect to one smart device. In this case, if a user carries multiple smart devices, multiple client terminals are needed to establish data connections with each smart device and perform data statistics respectively. However, the data statistics collected by the client terminals of the smart devices can be inconsistent, which may confuse the user.

SUMMARY

This disclosure provides a method of data statistics for wearable devices, which can merge physiological indicator data associated with the same statistical item of the same user from multiple wearable devices.

In an aspect, a method of method of integrating data from multiple wearable devices is provided. The method includes receiving, by a processor from a wearable device, physiological indicator data associated with a statistical item being collected for a user and a timestamp associated with the physiological indicator data, wherein the statistical item is collected by the wearable device, and determining, for the user, fused physiological indicator data associated with the statistical item based on, for each of the multiple wearable devices, a priority level, the physiological indicator data, and the timestamp associated with the physiological indicator data, wherein the multiple wearable devices comprise the wearable device and at least another wearable device associated with the user.

In another aspect, an apparatus for integrating data from multiple wearable devices is provided. The apparatus includes a processor and a memory coupled to the processor. The memory is configured to store instructions which when executed by the processor become operational with the processor to receive, from a wearable device, physiological indicator data associated with a statistical item being collected for a user and a timestamp associated with the physiological indicator data, wherein the statistical item is collected by the wearable device, and the physiological indicator data in the statistical item comprises at least one of: a step count, a movement distance, a heartbeat count, and an energy consumption value, and determine, for the user, fused physiological indicator data associated with the statistical item based on, for each of the multiple wearable devices, a priority level, the physiological indicator data, and the timestamp associated with the physiological indicator data, wherein the multiple wearable devices comprise the wearable device and at least another wearable device associated with the user, and the priority level for each of the multiple wearable device is determined based on at least one of: accuracy of the physiological indicator data collected by the wearable device and a predetermined priority level for the wearable device.

BRIEF DESCRIPTION OF THE DRAWINGS

This disclosure is best understood from the following detailed description when read in conjunction with the accompanying drawings. It will be apparent that the drawings in the following description are merely examples of this disclosure, and that other drawings can be obtained from the drawings without creative work. It is emphasized that, according to common practice, the various features of the drawings are not to-scale. On the contrary, the dimensions of the various features are arbitrarily expanded or reduced for clarity.

DETAILED DESCRIPTION

The technical solution in implementations of this disclosure will be described in detail below with reference to the accompanying drawings of examples of this disclosure. It is obvious that the described examples are merely part and not all of this disclosure. Based on the examples described herein, all other examples that are available without creative work are in the scope of this disclosure.

Through the technical solutions of this disclosure, the user can view unified physiological indicator data merged from different wearable devices, so as to effectively enhance the user experience of using the wearable device. A client terminal (or simply a "terminal") can connect to multiple wearable devices at the same time, and select a wearable device with the highest priority level for data synchronization, which can avoid un-unified data caused by simultaneous synchronization from the multiple devices. Also, when the data of the wearable synchronizing device is incomplete or null, the terminal can switch to a device with the next highest priority level for data synchronization, thus ensuring continuity of the data synchronization.

Figure 1:
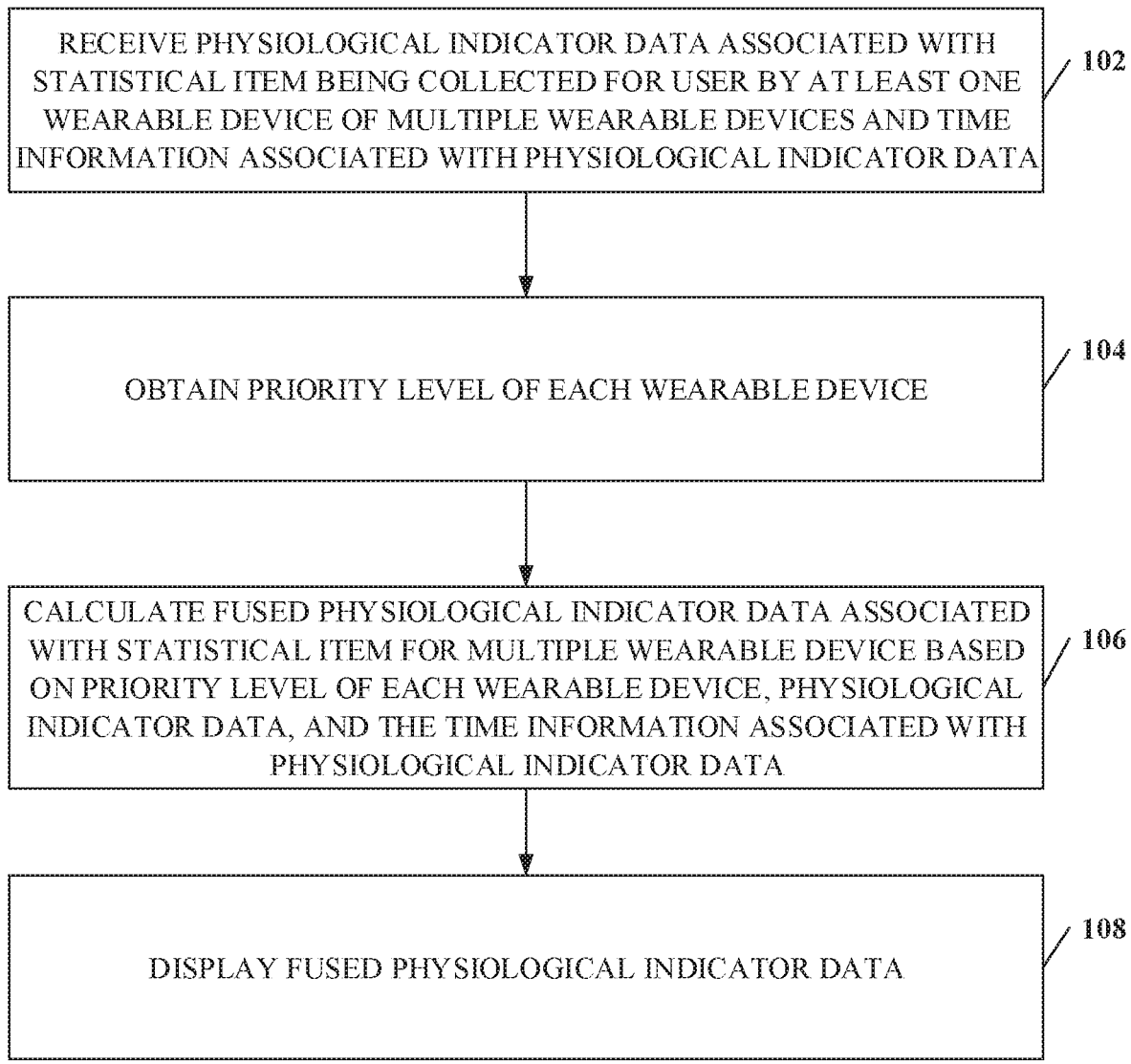
FIG. 1 is a flowchart of an example process for data statistics according to an implementation of this disclosure.

According to an implementation of this disclosure, a method of data statistics is provided. The method can be used for collecting or statistically analyzing data by a program and a terminal device including the program. As shown in FIG. 1, the method can include the following operations 102-108.

At operation 102, when multiple smart wearable devices (interchangeably referred to as "wearable devices," "smart devices," or simple "devices" hereinafter) are collecting physiological indicator data for a statistical item of a user, physiological indicator data and time information (e.g., a time point, a time period, a time interval, or a timestamp) associated with the physiological indicator data sent by at least one wearable device of the wearable devices are received. The "statistical item" herein refers to a group, a collection, a type, or a category of data for statistical analysis. For example, a statistical item can relate to a type of the physiological indicator data (e.g., a step count, a moving distance, a heart rate, an energy consumption value, or any combination thereof).

In an implementation, the physiological indicator data can include at least one of a step count (e.g., numbers of steps counted in walking or running), a movement distance, a heartbeat count (e.g., a heart rate), and an energy consumption value.

At operation 104, priority levels of the wearable devices are obtained. For example, each wearable device can have a priority level.

In an implementation, for a wearable device, the priority level can be determined based on a type of the wearable device.

At operation 106, fused physiological indicator data (or simply "fusion data") for the statistical item associated with the wearable devices is determined based on the priority level, the physiological indicator data and the time information associated with the physiological indicator data of each wearable device, The term "fuse" used herein can refer to fusing, integrating, aggregating, combining, merging, connecting, linking, coupling, associating, relating, attaching, accumulating, adding, compiling, uniting, unifying, mixing, mingling, or any action in any manner for using data or information from multiple data sources to determine, with or without manipulation thereof, one data representation or description of the data sources.

At operation 108, the fused physiological indicator data is displayed.

In this implementation, when physiological indicator data of a statistical item of a user is received by multiple smart devices, the physiological indicator data of the multiple smart devices with respect to the statistical item can be fused. The user can view the fused physiological indicator data. For example, the use can view a single data result displayed in a user interface (e.g., an interface of a software product or a phone application), which can improve user experience.

When the user has multiple wearable devices, the user can use the wearable devices separately or simultaneously. For example, the user can use a pair of smart running shoes for a first period of time, and then use a smart wristband for a second period of time. Typically, the user can view respective physiological indicator data corresponding to the two smart devices. According to implementations of this disclosure, the physiological indicator data of the two smart devices can be statistically analyzed and fused to determine fused physiological indicator data. If the user wants to view the fused physiological indicator data on a terminal (e.g., a smart phone), for example, the user can open an application in the terminal to synchronize (e.g., simultaneously or successively) the physiological indicator data received by the two smart devices to the terminal. The terminal can receive the physiological indicator data from the two smart devices and determine the fused physiological indicator data. In this example, the user can view unified physiological indicator data integrated or fused from different smart devices, which can improve the user experience.

In an implementation, the physiological indicator data can be stored in a dataset (e.g., an array, a vector, or a matrix) with a predetermined size or length. For example, each smart device can be associated with an array. Each element of the dataset can be associated with physiological indicator data received by the device at a temporal granularity (e.g., one minute). A temporal granularity can be used to specify the temporal qualification (or unit) of a set of data (e.g., in a database). For example, a temporal granularity of one minute can indicate that the received physiological indicator data is grouped in multiple records, in which each record includes physiological indicator data received within a minute. Temporal granularities can include milliseconds, seconds, minutes, hours, days, weeks, months, years, or any combination of any length of any time interval. In this implementation, the operation 106 can be: based on a priority level and an array associated with each smart device, determining a fused physiological indicator array associated with the fused physiological indicator data.

In an implementation, the physiological indicator data can be recorded at a temporal granularity of one minute. Each smart device can be assigned with an array with a predetermined size (e.g., an array of UINT8_T type with length 1408=24 h*60 min) for storing physiological indicator data received per minute (referred to as "per-minute physiological indicator data") by the smart device in a day. This array can be referred to as a "smart physiological indicator dataset." For example, after a minute, the smart device can store the per-minute physiological indicator data received within the minute into a corresponding element of the smart physiological indicator dataset.

In another implementation, each smart device can also be assigned with an array (referred to as a "smart device array") with a predetermined size (e.g., an array of UINT8_T type with a size 1408) in a corresponding terminal or application program. When a smart device connects to the terminal via wired or wireless connection, elements in a smart device array in the smart device can be transmitted to corresponding positions of a smart device array in the terminal via the connection. That is, the terminal can duplicate or copy the smart device array for each smart device.

Figure 2:
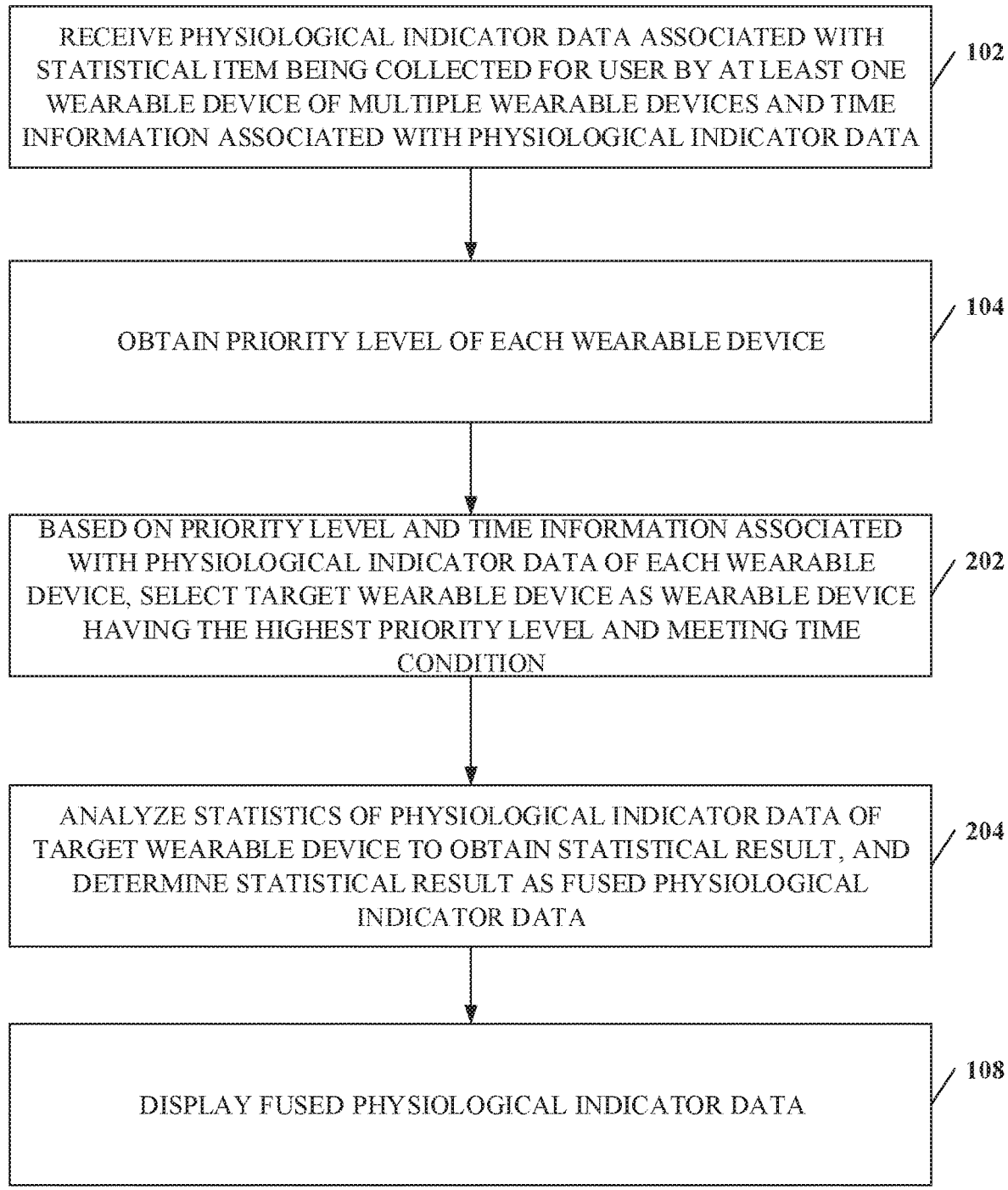
FIG. 2 is a flowchart of another example process for data statistics according to an implementation of this disclosure.

As shown in FIG. 2, in an implementation, the operation 302 includes operations 202-204.

At operation 202, based on the priority level and the time information associated with the physiological indicator data of each smart device, a smart device having the highest priority level and meeting a time requirement is selected as a target smart device.

At operation 204, physiological indicator data of the target smart device is statistically analyzed to obtain statistical results, which are determined as the fused physiological indicator data.

In this implementation, the smart device having the highest priority level and meeting the time requirement is selected as the target smart device based on the priority levels and the time information associated with the physiological indicator data of the smart devices. For example, the smart device can include a smart wristband, a smart watch, smart glasses, smart running shoes, or any combination of any smart wearable device. Typically, the smart devices can collect statistics of physiological indicator data (e.g., step counts, movement distances, heartbeat counts, or energy consumption values) of the user in independent processes. The user can manually set the priority levels for the smart devices based on accuracy of statistics data of each smart device. The priority levels of the smart devices can also be set by the terminal using default settings. For example, in accordance with a default setting, the priority levels of the smart devices can be from high to low as: smart running shoes>smart watch>smart wristband>smart glasses. When running. A corresponding client terminal can automatically monitor whether physiological indicator data of a statistical item for the user is being received through multiple smart devices. When the physiological indicator data of the statistical item for the user is detected to be received through the multiple smart devices, by determining the priority level and time information of each smart device, a smart device having the highest priority level and meeting the time requirement can be determined as the target smart device.

In some implementations, there can be multiple data synchronization modes. For example, the data synchronization modes can include a realtime synchronization mode, in which statistics of the data collected by the smart device can be synchronized to the client terminal in realtime. In an implementation, for example, when a user opens an application in a phone as the user walks, a total step count can be updated and displayed in the application in realtime. For another example, the data synchronization modes can include a non-realtime synchronization mode, in which the statistics of the data collected by the smart device can be synchronized to the client terminal at a predetermined time. In an implementation, for example, when the user opens the application in the phone after using the smart devices for a period of time, the application can synchronize historical data from the smart devices and display it in a user interface (e.g., a page for history details). The user can choose any data synchronization mode in accordance with needs and scenarios. Based on the selected data synchronization mode, the statistics of the data collected by the determined target smart device can be synchronized, and the synchronized data can be displayed. The "historical data" herein refers to physiological indicator data received by a wearable device in time periods earlier than a current time.

In an implementation, when the physiological indicator data in the target smart device is incomplete (e.g., not received or not transmitted) or null (e.g., empty or containing all zeros), a smart device having the next highest priority level and meeting the time requirement can be determined as a new target smart device. Statistics of physiological indicator data can be collected from the new target smart device to determine the fused physiological indicator data.

Figure 3:
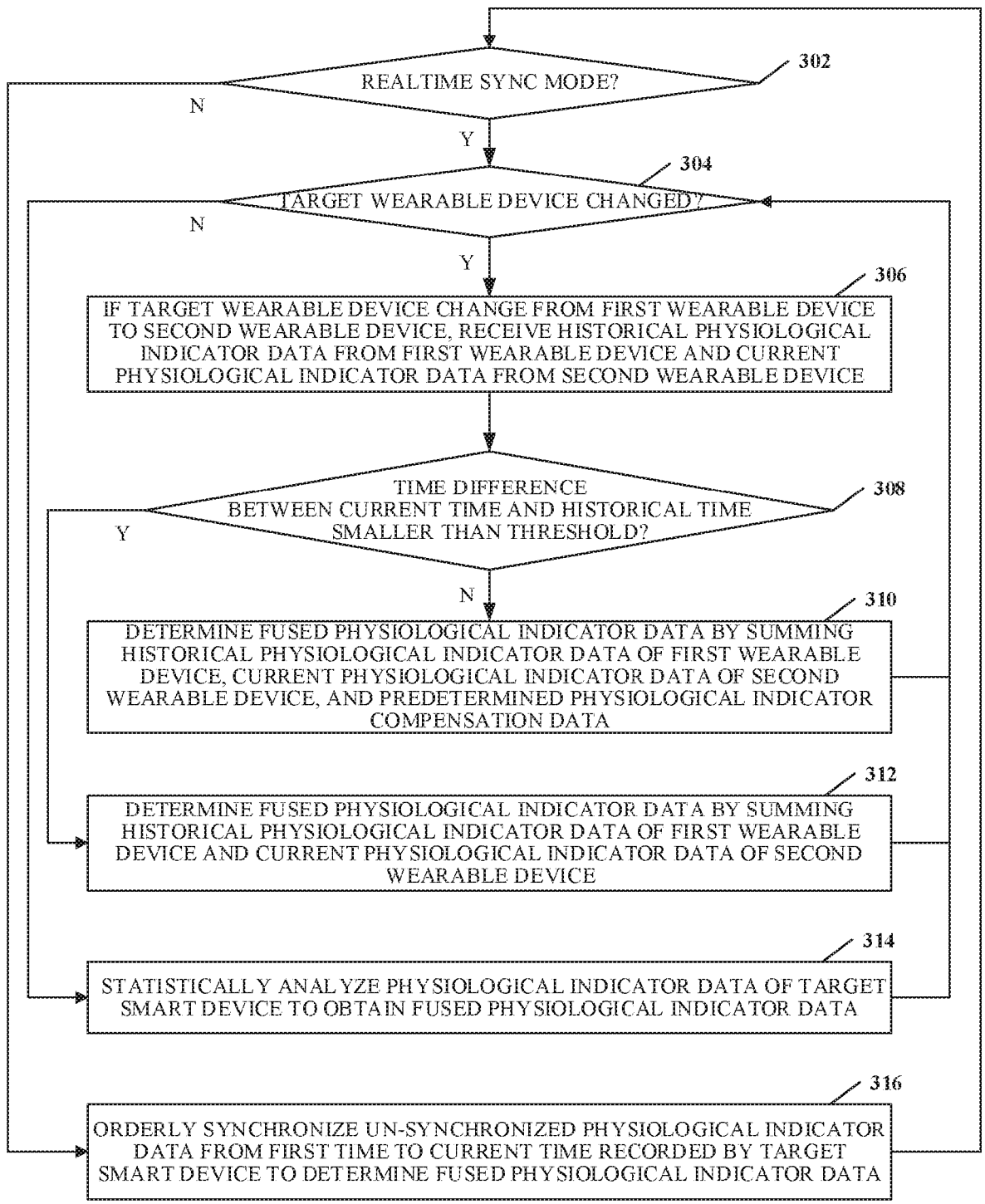
FIG. 3 is a flowchart of an example process for data synchronization according to an implementation of this disclosure.

As shown in FIG. 3, the operation 204 can include operations 302-316.

At operation 302, it is determined whether a current data synchronization mode is a realtime synchronization mode or a non-realtime synchronization mode. If the current data synchronization mode is the realtime synchronization mode, operation 304 is performed. If the current data synchronization mode is the non-realtime synchronization mode, operation 316 is performed.

At the operation 304, it is determined whether the target smart device is changed. If the target smart device is changed, operation 306 is performed. Otherwise, operation 314 is performed.

At the operation 306, if the target smart device is changed from a first smart device to a second smart device, historical physiological indicator data recorded by the first smart device and current physiological indicator data of the second smart device are received.

In an implementation, for example, in the realtime synchronization mode, when the target smart device is detected to change from a smart wristband to smart running shoes, based on the historical physiological indicator data recorded by the smart wristband and the current physiological indicator data of the smart running shoes, the fused physiological indicator data can be determined.

In some cases, when a time difference exists between a current time and a historical time corresponding to the historical physiological indicator data of the first smart device, the historical physiological indicator data of the first smart device and the current physiological indicator data of the second smart device can be discontinuous. If the time difference is smaller than a predetermined threshold (e.g., 5 seconds), the time difference can be ignored, and it can be determined that the impact of the discontinuity (or disconnect) to the fused physiological indicator data is relatively small. If the time difference is greater than or equal to a predetermined threshold (e.g., 5 seconds), it can be determined that the impact of the discontinuity to the fused physiological indicator data is relatively large, and predetermined physiological indicator data can be used to compensate the discontinuity to ensure accuracy of the fused physiological indicator data.

At operation 308, it is determined whether the time difference between the current time and the historical time corresponding to the historical physiological indicator data of the first smart device is smaller than the predetermined threshold.

At the operation 310, when the time difference is greater than or equal to the predetermined threshold, the historical physiological indicator data recorded by the first smart device, the current physiological indicator data of the second smart device, and the predetermined physiological indicator data for compensation can be added or summed to obtain the fused physiological indicator data.

At operation 312, when the time difference is smaller than the predetermined threshold, the historical physiological indicator data recorded by the first smart device and the current physiological indicator data of the second smart device can be added or summed to obtain the fused physiological indicator data.

At the operation 314, the physiological indicator data of the target smart device can be statistically analyzed to obtain the fused physiological indicator data.

At the operation 316, un-synchronized physiological indicator data from the first time (referred to as a "first un-synchronized time") or the earliest time for which no synchronization has been performed to the current time recorded by the target smart device is orderly synchronized to determine the fused physiological indicator data.

For example, the order can include a backward order (from a later time to an earlier time), in which the data is synchronized backwardly starting from the current time to the first un-synchronized time.

Implementations and processes for data fusion is set forth in the following description using examples of step counts. These implementations and processes can also apply to data fusion of other types of physiological indicator data.

In an implementation, a storage format can be defined for a step count. Each smart device can use an independent dataset (e.g., an array) to store step counts for a day. For example, each stored step count can be for a minute (referred to as a "per-minute step count"). For example, the dataset (e.g., the array) can have a size of 1408 (1408=24 h*60 min). A step count after data fusion (referred to as a "fused step count") can be stored in another independent dataset (e.g., an array) with the size 1408. Each smart device can include an independent total step count for the device. For example, the fused total step count can be displayed in an application of a phone after integrating total step counts of multiple smart devices up to a current time.

In an implementation, a priority level can be predetermined for a smart device. For example, when physiological indicator data is received from multiple smart devices, it can be prioritized that what physiological indicator data from which smart device will be synchronized to the client terminal for display. Typically, smart running shoes can count steps more accurately than a smart wristband. In an example, when step count data is transmitted to a phone simultaneously from a smart wristband and a pair of smart running shoes, the phone can prioritize to synchronize and display the step count from the smart running shoes.

The following description will set forth data storage formats of multiple devices, including total step counts, step counts per minute for a device, fused step counts per minute, and data synchronization parameters.

In an implementation, a value indicative of a total step count can be assigned for each smart device. For example, when the total step count changes, the smart device can broadcast its value indicative of the total step count wirelessly (e.g., via Bluetooth), and a phone can receive and store the value. The value can be referred to as a "total step count of a device." For example, a total step count for a pair of smart running shoes can be referred to as a "total step count of smart running shoes."

In an implementation, a value indicative of a processed total step count can be stored in the phone. For example, the phone can display only one total step count based on the value. The value can be referred to as a "fused total step count." In an example, when the user wears only one smart device, the value of the fused total step count can be equal to the value of the total step count of the device.

In some cases, the user may want to know details of step counts displayed with time information. For those cases, after a period of time (e.g., a minute), step counts within the period of time can be stored.

For example, historical data can be recorded at a temporal granularity of one minute. In a smart device, a dataset (e.g., an array of UINT8_T type) with a size (e.g., 1408=24 h*60 min) can be assigned to record per-minute step counts received by the smart device in a day. The dataset (e.g., the array) can be referred to as a "per-minute step count dataset of a device," or simply a "physiological indicator dataset of a device." For example, the physiological indicator dataset of a device can include a set of elements or storage spaces (e.g., one or more bits in a non-transitory computer-readable medium), in which each element can be used to store a portion of the physiological indicator data received by the device within a period of time (e.g., a minute, multiple minutes, a day, or any time interval). The set of elements can be associated with a temporal granularity. For example, if the physiological indicator data are received at a temporal granularity of one minute, each element of the physiological indicator dataset of the device can store a record of per-minute physiological indicator data received by the device.

The physiological indicator dataset can include any form of any set of data. For example, the physiological indicator dataset can be in a form of an array, a list, a vector, a matrix, a string of characters, a binary file, a text file, a database entry, a sequence, a graph, or any other suitable form of data collection. If the physiological indicator dataset is in a form of an array, the per-minute step count dataset of the device can be referred to as a "device array" or "physiological indicator array." For ease of explanation without causing any ambiguity, the "physiological indicator array" is used as an example implementation of the physiological indicator dataset hereinafter, and does not limit or preclude other possible implementations. It should be understand that various implementations of the physiological indicator dataset can be derived from this disclosure without creative work.

After a minute, for example, the device can store the step count in the minute in a corresponding element of the physiological indicator dataset. In the phone, a dataset (e.g., an array of UINT8_T type) with a size (e.g., 1408) can also be assigned for each device. When a smart device connects to the phone wirelessly (e.g., via Bluetooth) or via another type of connection for data synchronization, un-synchronized records in a physiological indicator array in the smart device can be transmitted to corresponding records of a physiological indicator array in the phone. That is, the phone can duplicate or copy the physiological indicator array from each smart device.

Starting from a record corresponding to a first minute in the physiological indicator array, values of the records in the physiological indicator array can be summed to determine a record corresponding to a current minute or a minute closest to a current time. The summed value can indicate a total step count for the physiological indicator array, which can be referred to as a "physiological indicator array sum."

In an implementation, after per-minute step counts are recorded into corresponding records of the physiological indicator array, the total step count of the device can be equal to the physiological indicator array sum. During other time, the total step count of the device can be slightly larger than the physiological indicator array sum, because a step count in a minute has been counted into the total step count of the device before the minute ends, but might not has been counted into the physiological indicator array sum.

Correspondingly, for example, in the phone, a dataset (e.g., an array of UINT8_T type) with the same size (e.g., 1408) can also be stored to record a per-minute step count fused from multiple devices. The dataset can be referred to as a "fused per-minute step count dataset," or simply a "fused physiological indicator dataset." For example, the fused physiological indicator dataset can include a set of elements or storage spaces (e.g., one or more bits in a non-transitory computer-readable medium), in which each element can be used to store a portion of the fused physiological indicator data within a period of time (e.g., a minute, multiple minutes, a day, or any time interval). The set of elements can be associated with the temporal granularity used by the devices. For example, if the devices use a temporal granularity of one minute, each element of the fused physiological indicator dataset can store a record of per-minute fused physiological indicator data fused using physiological indicator data received by the devices within that minute.

Similar to the physiological indicator dataset and the physiological indicator array, the fused physiological indicator dataset can include any form of any set of data. If the fused physiological indicator dataset is in a form of an array, the fused physiological indicator dataset can be referred to as a "fusion array" or "fused physiological indicator array." For ease of explanation without causing any ambiguity, the "fused physiological indicator array" is used as an example implementation of the fused physiological indicator dataset hereinafter, and does not limit or preclude other possible implementations. It should be understand that various implementations of the fused physiological indicator dataset can be derived from this disclosure without creative work.

In an implementation, after the phone receives multiple physiological indicator arrays, fused per-minute step counts can be recorded into corresponding positions in the fused physiological indicator array. The fused per-minute step counts can be used to display the total step count and/or time-wise exercise details in an application of the phone.

In an implementation, in the phone, an additional dataset (e.g., an array of UINT8_T type) with the same size (e.g., 1408) can also be stored. Each record of the additional dataset can be used to record synchronization data corresponding to a minute. The synchronization data can include a synchronization mode, a parameter (e.g., a flag) indicative of data integrity (referred to as a "data integrity parameter"), a device identifier, or any other information related to synchronization. The additional dataset can be referred to as a "flag dataset." Based on obtained device identifiers of the devices, synchronization modes (e.g., realtime synchronization modes or non-realtime synchronization modes) between the client terminal and each device, and data integrity parameters recorded and stored for each time interval of a temporal granularity (e.g., one minute), the flag dataset (e.g., an array) can be assigned to the client terminal. For example, the flag dataset can include a set of elements or storage spaces (e.g., one or more bits in a non-transitory computer-readable medium), in which each element can be used to store one or more parameters (referred to as "flags") within a period of time (e.g., a minute, multiple minutes, a day, or any time interval). The set of elements can be associated with the temporal granularity used by the devices. For example, if the devices use a temporal granularity of one minute, each element of the flag dataset can store a record of per-minute flag data associated with synchronization for the devices within that minute.

Similar to the physiological indicator dataset and the physiological indicator array, the flag dataset can include any form of any set of data. If the flag dataset is in a form of an array, the flag dataset can be referred to as a "flag array." For ease of explanation without causing any ambiguity, the "flag array" is used as an example implementation of the flag dataset hereinafter, and does not limit or preclude other possible implementations. It should be understand that various implementations of the flag dataset can be derived from this disclosure without creative work.

For example, in a flag array, a first set size (e.g., 5 bits) can be used for device identifiers indicative of the devices worn by the user. In an example, a device identifier can include values 0 indicative of "no device," 1 indicative of "a smart wristband," 2 indicative of "smart running shoes," 3 indicative of "a smart watch," and so on.

For another example, in the flag array, a second set size (e.g., 2 bits) can be used for synchronization modes indicative of means for synchronizing data between the client terminal and the devices. In an example, a synchronization mode can include values 0 indicative of "un-synchronized" (not yet synchronized), 1 indicative of "non-realtime synchronization," 2 indicative of "real-time synchronization," 3 indicative of "compensation synchronization," and so on.

For another example, in the flag array, a third set size (e.g., 1 bit) can be used for data integrity parameters indicative of whether the recorded and stored data is complete. In an example, a data integrity parameter can include values 0 indicative of "data incomplete," 1 indicative of "data complete," and so on.

An advantage of the flag dataset is that, if abnormality occurs when the client terminal is fusing data or generating the fused physiological indicator dataset, the fused physiological indicator dataset can be reset based on the flag dataset to minimize data lost.

For example, Table 1 shows a data storage format in the client terminal (e.g., a phone) when a user wearing a smart wristband and smart running shoes finishes data synchronization at a time (e.g., 9:31:15).

TABLE 1

| Flag Array | 1-1-1 | 1-1-1 | ... | 1-1-1 | 1-1-2 | 1-1-2 | ... | 1-1-2 | 1-0-1 | ... | 0-0-0 |
|---|---|---|---|---|---|---|---|---|---|---|---|
| Sync Mode | NR | NR | ... | NR | NR | NR | ... | NR | U | ... | U |
| Data Integrity | Y | Y | ... | Y | Y | Y | ... | Y | N | ... | N |
| Device ID | W | W | ... | W | S | S | ... | S | W | ... | N |

In Table 1, the first row shows flag arrays for the synchronization data. Each flag array includes three elements: the first element indicates a synchronization mode; the second element indicates data integrity; and the third element indicates a device identifier.

The second row shows specific meanings for the value of the synchronization mode element in each flag array: "NR" indicates a non-realtime synchronization mode; and "U" indicates data un-synchronized. In Table 1, "1" as the first element value of each flag array indicates the non-realtime synchronization mode, and "0" as the first element value of each flag array indicates that the data of the minute is un-synchronized.

The third row shows specific meanings for the value of the data integrity element in each flag array: "Y" indicates the per-minute step count is complete; "N" indicates the per-minute step count incomplete. In Table 1, "1" as the second element value of each flag array indicates the per-minute step count is complete, and "0" as the second element value of each flag array indicates the per-minute step count incomplete.

The fourth row shows specific meanings for the value of the device identifier element in each flag array: "W" indicates a smart wristband is used as the target smart device to generate the fused physiological indicator data for the minute; "S" indicates a pair of smart running shoes are used as the target smart device to generate the fused physiological indicator data for the minute; and "N" indicates there is no target device (e.g., the user is not wearing any smart device). In Table 1, "1" as the third element value of each flag array indicates the target device is the smart wristband, "2" as the second element value of each flag array indicates the target device is the smart running shoes, and "0" as the third element value of each flag array indicates there is no target device.

In an implementation, as shown in Table 2, a temporal granularity between the client terminal and each device can be predetermined as one minute. A physiological indicator array of UINT8_T type with a size 1408 (1408=24 h*60 min) can be assigned for the client terminal. A physiological indicator array of the UINT8_T type with the size 1408 can also be assigned for each device. The physiological indicator arrays for the client terminal and the devices can be used to record per-minute step counts recorded by each device for a user in a day.

Table 2 shows a data storage format in the client terminal (e.g., a phone) when a user wearing a smart wristband and smart running shoes finishes data synchronization at a time (e.g., 9:31:15).

TABLE 2

| Sequence | 1 | 2 | ... | 508 | 541 | 542 | ... | 571 | 572 | ... | 1408 |
|---|---|---|---|---|---|---|---|---|---|---|---|
| Time | 00:00 | 00:01 | ... | 8:59 | 9:00 | 9:01 | ... | 9:30 | 9:31 | ... | 23:59 |
| Event | | | | | Shoes On | | | Shoes Off | Sync | | |
| Wristband Array | 20 | 30 | ... | 30 | 35 | 210 | ... | 98 | 0 | ... | 0 |
| Wristband Array Sum | 20 | 50 | ... | 330 | 365 | 575 | ... | 5000 | | | |
| Wristband Total Steps | | | | | | | | | 5010 | | |
| Shoe Array | 0 | 0 | ... | 0 | 30 | 200 | ... | 90 | 0 | ... | 0 |
| Shoe Array Sum | 0 | 0 | ... | ... | 30 | 230 | ... | 1500 | | | |
| Shoe Total Steps | | | | | | | | | 1500 | | |
| Fusion Array | 20 | 30 | ... | 30 | 30 | 200 | ... | 90 | 10 | ... | 0 |
| Fusion Array Sum | 20 | 50 | ... | 330 | 360 | 560 | ... | 4800 | | | |
| Fused Total Steps | | | | | | | | | 4810 | | |

In Table 2, the first row shows sequence numbers for array elements starting from 1 to 1408, each sequence number corresponding to a minute.

The second row shows a start time of each minute.

The third row shows a user event occurring in each minute, such as, for example, putting on shoes, taking off shoes, or syncing data.

The fourth row shows values of the physiological indicator array for the smart wristband (referred to as the "wristband array").

The fifth row shows time-dependent changes of values of the physiological indicator array sum for the smart wristband (referred to as the "wristband array sum").

The sixth row shows the total step count of the device for the smart wristband when the synchronization finishes.

The seventh row shows values of the physiological indicator array for the smart running shoes (referred to as the "shoe array").

The eighth row shows time-dependent changes of values of the physiological indicator array sum for the smart running shoes (referred to as the "shoe array sum").

The ninth row shows the total step count of the device for the smart running shoes when the synchronization finishes.

The tenth row shows values of the fused physiological indicator array after fusing the wristband array and the shoe array.

The eleventh row shows time-dependent changes of values of the fused physiological indicator array sum.

The twelfth row shows the fused total step count when the synchronization finishes. It is possible that the fused total step count is slightly larger than the fused physiological indicator array sum, because the fused total step count includes a difference between the total step count of the device (e.g., the smart wristband) and the device (e.g., the wristband) array sum.

In the 30 minutes of 9:00-9:30, the user is wearing the smart running shoes for running, during when a data connection establishes between the client terminal (e.g., the phone) and the smart running shoes. In other time periods, the user is not wearing the smart running shoes, during when the established data connection between the client terminal and the smart running shoes disconnects. Therefore, the step counts of the shoe array are non-zero only during the 30 minutes, and are all zeroes during other time. Based on predetermined priority levels of each device for synchronization, the fused physiological indicator array can choose to synchronize the step count data of the smart running shoes during the 30 minutes of 9:00-9:30, and to synchronize the step count data of the smart wristband during other time periods. The total step count for display can be the fused total step count.

The following description will set forth means for connecting and synchronizing data between a wearable device and a phone, including non-realtime synchronization, real-time synchronization, and means for keeping the connection.

In some implementations, a smart device can communicate with a phone via Bluetooth for data synchronization. The data synchronization can include two modes, a non-realtime synchronization mode and a realtime synchronization mode.

For example, the non-realtime synchronization mode can be used for the user to view exercise details of the day after wearing one or more smart devices for a period of time. For example, when the user opens an application in the phone, the phone starts to establish a connection to a smart device. Alternatively, the phone can also starts to establish the connection when the user performs a pull-to-refresh operation in an interface of the application. When the connection is established, the device can transmit stored historical data (e.g., per-minute data) to the phone. For example, the phone can retrieve all of the historical data from the device to process for display in an interface for the exercise details on the phone.

In an implementation, in the non-realtime synchronization mode, at least two types of data can be transmitted from multiple devices: physiological indicator arrays and total step counts of the devices. After receiving multiple physiological indicator arrays and total step counts of the devices, the phone can configure a fused physiological indicator array in accordance with the non-realtime synchronization and display a fused total step count.

Table 3 shows example synchronization information between a phone and a smart wristband when non-realtime synchronization occurs at a time (e.g., 9:31:15).

TABLE 3

| Sequence Number | 1 | 2 | ...... | 571 | 572 | 573 | ... | 1408 |
|---|---|---|---|---|---|---|---|---|
| Time | | | ...... | 9:30 | 9:31 | 9:32 | ... | 23:59 |
| Event | | | | | Sync | | | |
| Wristband Array in Wristband | 20 | 30 | ...... | 98 | 0 | 0 | ... | 0 |
| Wristband Array Sum in Wristband | 20 | 50 | ...... | 5098 | | | | |
| Wristband Total Steps in Wristband | | | | | 6000 | | | |
| Sync and Process | ↓ | ↓ | ↓ | ↓ | | | | |
| Wristband Array in Phone | 20 | 30 | ...... | 98 | 0 | 0 | ... | 0 |
| Wristband Array Sum in Phone | 20 | 50 | ...... | 5098 | | ... | | |
| Wristband Total Steps in Phone | | | | | 6000 | | | |

For example, the realtime synchronization mode can be used or such a scenario: when the user opens the application and establishes the connection to the device, if the user leaves the application running (e.g., after finishing the non-realtime synchronization) and the total step count of the device continues to change, the total step count of the device can be displayed on the phone in realtime after being broadcasted by the device and received by the phone. For example, the realtime synchronization mode can allow the user to view the changing total step count displayed on the phone in realtime as the user walks. For another example, the realtime synchronization mode can allow the user to check whether the step count function of the device is accurately performed.

In the realtime synchronization mode, when receiving total step counts of multiple devices, the phone can configure a fused physiological indicator array in accordance with the realtime synchronization and display a fused total step count.

In some implementations, the realtime synchronization can be performed only after the non-synchronization having been performed for at least once.

In some implementations, to keep the realtime connection between the device and the phone, a connection packet can be broadcasted by the device at short time intervals (e.g., every two seconds). For example, the connection packet can include a MAC address of the device. For another example, the connection packet can only include the MAC address of the device without any step count data.

When no connection packets is received after a certain period of time, for example, it can be determined that the device has disconnected to the phone. In some cases, the connection can be re-established.

The following description will set forth priority levels for synchronizing multiple devices.

When the user wears multiple devices, for example, each device can duplicate its physiological indicator array storing step counts to the phone during data synchronization. When generating a fused physiological indicator array, based on predetermined priority levels of the devices, it can be determined for a current minute that which device is prioritized to duplicate its data into the fused physiological indicator array.

For example, smart running shoes can generate accurate step counts because they can be set to count the steps only when touching the ground. A smart wristband or a smart watch might generate relatively inaccurate step counts because they count the steps mainly by counting arm swings. Therefore, when fusing the step count data, for example, the smart running shoes can be set with the highest priority level. In addition, in some implementations, the smart watch can use more sophisticated techniques or processes to improve accuracy of step counting. When fusing the step count data, for example, the smart watch can be set with the next highest priority level. In an implementation, when synchronizing data, the priority levels of step counting devices can be set from low to high as: smart wristband<smart watch<smart running shoes.

The following description will set forth synchronization processes for multiple devices, including non-realtime single-device or multi-device synchronization processes and realtime single-device or multi-device synchronization processes.

The non-realtime synchronization processes can be simpler compared with the realtime synchronization processes. The non-realtime synchronization processes can be used to fuse historical data from physiological indicator arrays to a fused physiological indicator array for displaying exercise details. The following description will set forth example processes for synchronization between a single device and a phone, example processes for synchronization between multiple devices and the phone, and example implementations for special cases.

For non-realtime single-device synchronization, the "single-device" does not mean that a user can only wear one device, but means that the non-realtime synchronization is performed between a single device and the phone in a period of time.

There can be various processes to synchronize historical data from a physiological indicator array of a single device to a fused physiological indicator array. Assuming the single device having a sequence number N, the synchronization processes can comply with some example principles described as follows.

Principle A1: "reverse chronological order" or "from near to far"

For example, the data is synchronized in a reverse order in time, from the latest minute to the earliest minute of which the data has not been synchronized (referred to as "the first un-synchronized minute"). For example, the synchronization operations can include: a step count of a minute in the physiological indicator array can be copied to a position in the fused physiological indicator array corresponding to the minute; "1-1-N" can be stored in the flag array for the minute, indicative of "non-realtime synchronization," "data complete," and "the synchronizing device having sequence number N," respectively; and the step count in the minute can be added to the fused physiological indicator array sum. More details of principle A1 will be described in later description.

Principle A2: "first come first served"

For example, if the element in the flag array has been assigned with values and the step count in the minute is non-zero, when the data integrity element in the flag array is "1," it can be determined that the data (step count) in the minute is complete, and can be skipped for synchronization.

Principle A3: "replacing elements with zero step count"

For example, if the element in the flag array has been assigned with values but the step count in the minute is zero, a replacing operation can be performed, including: the step count in the minute in the physiological indicator array can be copied to the position in the fused physiological indicator array corresponding to the minute; "1-1-N" can be stored in the flag array for the minute, indicative of "non-realtime synchronization," "data complete," and "the synchronizing device having sequence number N," respectively; and the step count in the minute can be added to the fused physiological indicator array sum.

Principle A4: "compensating incomplete realtime data"

For example, if the element in the flag array has been assigned with values "2-0-M," it can indicate that: the realtime synchronization has been performed for the minute; the data is incomplete; and the previous synchronizing device has a sequence number M. A possible cause for such values in the flag array can be: when the realtime synchronization was performing for the minute, the device lost the connection before finishing the synchronization (e.g., the application was closed). More details of possible causes for such flag values will be described in later description.

For another example, if the device sequence number M=N, and the step count in the minute in an element of the physiological indicator array is larger than the step count in the minute in a corresponding element of the fused physiological indicator array, the synchronization can include operations to change the arrays as follows: the element of the fused physiological indicator array can be replaced by the element of the physiological indicator array; "3-1-N" can be stored in the flag array for the minute, indicative of "non-realtime synchronization data compensating realtime synchronization data," "data complete," and "the synchronizing device having sequence number N," respectively; and a difference between the element of the physiological indicator array and the corresponding element of the fused physiological indicator array can be added to the fused physiological indicator array sum. In an implementation, no further changes are made to the arrays.

Principle A5: "compensating fused total step count"

Typically, the non-realtime synchronization is performed at a time point within a minute. For example, data before 9:30:00 is being synchronized at 9:30:30. In the 30 seconds of 9:30:00-9:30:30, if the physiological indicator array stores the step count of the minute when the minute ends, a partial step count can be generated but has not stored in the physiological indicator array yet. In this example, to include the partial step count generated within the 30 seconds in the fused total step count, after finishing synchronization of all per-minute data, the phone can receive the total step count of the device and reset the fused total step count. For example, the fused total step count can be determined using Eq. (1):

$$\text{fused total step count} = \text{fused physiological indicator array sum} + \text{total step count of the device} - \text{synchronized physiological indicator array sum}$$

In some implementations, priority levels can be used for the compensating operations in principle A5. For example, after devices with higher priority levels are used to compensate the fused total step count, devices with lower priority levels can be skipped for the compensating operations.

For non-realtime multi-device synchronization, the synchronization processes can comply with some example principles described as follows.

When the user has multiple devices, the following scenario can be typical: the user wears the smart running shoes and the smart wristband for a time period, and opens the application to simultaneously synchronize exercise data from the two devices to the phone. In this example scenario, the phone can simultaneously receive two physiological indicator arrays.

Based on the following principles, simultaneous synchronization for multiple devices can be converted to sequential synchronization that can use the single-device synchronization principles.

Principle A6: "higher priority first"

According to principle A6, devices with higher priority levels can be synchronized first, followed by devices with lower priority levels.

In an implementation, for the above-described non-realtime single-device synchronization processes, the data can be set to be synchronized in the reverse chronological order starting from the latest minute. A reason for applying such process can be that, a clock of the phone can be inconsistent with a clock of the device. For example, the phone and the device can use different chips having different clock cycles. After a certain time period, the time of the phone and the time of the device can be different (e.g., offset for a few seconds or a few minutes). The inconsistent times can cause the physiological indicator array of the device and the physiological indicator array of the phone being misaligned for synchronization.

To avoid the possible inconsistent times, the synchronization can start from the latest minute, which is based on an assumption: the latest minute of the device corresponds to the latest minute of the phone.

For example, when the time of the phone leads the time of the device for 1 minute (e.g., a current time of the phone is 9:31:15 and a current time of the device is 9:30:35), a synchronization process as shown in Table 4 can be used.

TABLE 4

| Sequence Number | | 1 | 2 | ... ... | 571 | 572 | 573 | ... | 1408 |
|---|---|---|---|---|---|---|---|---|---|
| | Time | | | ... ... | 9:30 | 9:31 | 9:32 | ... | 23:59 |
| | Event | | | | | Sync | | | |
| Wristband | Wristband Array | 20 | 30 | ... ... | 98 | 0 | 0 | ... | 0 |
| | Wristband Array Sum | 20 | 50 | ... ... | 5098 | | | | |
| | Wristband Total Steps | | | | | 6000 | | | |
| Sync and Process | | ↘ | ↘ | ↘ | ↘ | | | | |
| Phone | Wristband Array | 0 | 20 | 30 | ... | 98 | 0 | 0 | ... | 0 |
| | Wristband Array Sum | 0 | 20 | 50 | ... | 5098 | | | ... | |
| | Wristband Total Steps | | | | | | 6000 | | | |

For another example, when the time of the phone lags the time of the device for 1 minute (e.g., the current time of the phone is 9:31:15 and the current time of the device is 9:32:35), a synchronization process as shown in Table 5 can be used.

TABLE 5

| | Sequence Number | 1 | 2 | ... | ... | 571 | 572 | 573 | ... | 1408 |
|---|---|---|---|---|---|---|---|---|---|---|
| | Time | | | ... | ... | 9:30 | 9:31 | 9:32 | ... | 23:59 |
| | Event | | | | | | Sync | | | |
| Wristband | Wristband Array | 20 | 30 | ... | | 98 | 90 | 100 | 0 ... | 0 |
| | Wristband Array Sum | 20 | 50 | ... | | 5098 | 5188 | 5288 | | |
| | Wristband Total Steps | | | | | | | 5060 | | |
| | Sync and Process | Discard | ✓ | ✓ | ✓ | ✓ | ✓ | ✓ | | |
| Phone | Wristband Array | | 30 | ... | | 98 | 90 | 100 | 0 ... | 0 |
| | Wristband Array Sum | | 50 | ... | | 5098 | 5188 | 5288 | | |
| | Wristband Total Steps | | | | | | | 5060 | | |

In some implementations, when the time of the device jumps to a next minute, the device can store the step count of a previous minute. When the time of the phone jumps to the next minute, the phone can generate a new storage space (e.g., a new element in the physiological indicator array in the phone) to store the step count of the device. If the time of the phone and the time of the device is inconsistent, they jump to the next minute at different time points. For such a scenario, it can be set in an implementation that: when the phone has new per-minute data of the fused physiological indicator array available to be stored and the device has newly stored un-synchronized physiological indicator array data, non-realtime synchronization according to the principles A1-A5 is performed; otherwise, the non-realtime synchronization is performed only according to the principle A5—that is, only the fused total step count will be changed according to the Eq. (1).

According to the design for the non-realtime data synchronization in this disclosure, based on the principle A6, a device with higher priority levels can be prioritized to synchronize its data to the fused physiological indicator array. However, in a minute, if a device with a higher priority level generates a smaller step count (e.g., due to usage for a very short time period) and a device with a lower priority level generates a larger step count, based on the principle A6, the step count generated by the device with the lower priority level cannot be synchronized into the fused physiological indicator array, which can cause the fused step count less than expected.

For example, a user takes off the smart running shoes at 9:31:05. In the first 5 seconds in the minute 9:31, the smart running shoes can generate a step count of 16. For the remaining 55 seconds, the smart wristband can generate a step count of 100. When performing the non-realtime synchronization, if the smart running shoes are being synchronized first or the smart running shoes and the smart wristband are being simultaneously synchronized, based on the principle A6, the step count of 16 will be stored into an element of the fused physiological indicator array corresponding to the minute 9:31. In addition, based on the principle A6, the step count of 100 generated by the smart wristband cannot be stored into the fused physiological indicator array, which can cause the step count in the minute 9:31 less than expected.

Typically, the above scenario happens only in the minute when the devices are changed, and the user is usually unaware of whether the data in the minute is consistent with expectation, the above scenario can have insignificant effect on user experience.

An example of the non-realtime synchronization is described as follows.

In an implementation, if the user wears the smart wristband and the smart running shoes, when the client terminal is performing the non-realtime data synchronization, each type of the data can be shown in Table 6.

TABLE 6

| Sequence Number | 1 | ... | 541 | 542 | ... | 552 | 553 | 554 | ... | 572 |
|---|---|---|---|---|---|---|---|---|---|---|
| Time | 00:00 | ... | 9:00 | 9:01 | ... | 9:11 | 9:12 | 9:13 | ... | 9:31 |
| Event | | | Shoes On | App Opened | | App Closed | Shoes Off | | | App Opened |
| Wristband Array | 20 | ... | 100 | 100 | ... | 105 | 100 | 100 | ... | 0 |
| Wristband Array Sum | 20 | ... | 365 | 465 | ... | 1600 | 1700 | 1800 | ... | 5040 |
| Wristband Total Steps | | | | | | | | | | 5250 |
| Shoe Array | 0 | ... | 30 | 90 | ... | 100 | 20 | 0 | ... | 0 |

TABLE 6-continued

| Sequence Number | 1 | ... | 541 | 542 | ... | 552 | 553 | 554 | ... | 572 |
|---|---|---|---|---|---|---|---|---|---|---|
| Shoe Array Sum | 0 | ... | 30 | 120 | ... | 1200 | 1220 | 1220 | ... | 1220 |
| Shoe Total Steps | | | | | | | | | | 1220 |
| Fusion Array | 20 | ... | 30 | 90 | ... | 100 | 20 | 100 | ... | 0 |
| Fusion Array Sum | 20 | ... | 360 | 450 | ... | 1506 | 1550 | 1650 | ... | 5050 |
| Fused Total Steps | | | | | | | | | | 5020 |
| Flag Array | 1-1-1 | ... | 1-1-2 | 2-1-2 | ... | 3-1-2 | 1-1-2 | 1-1-1 | ... | 0-0-0 |
| Sync Mode | NR(1) | ... | NR(1) | R(2) | ... | C(3) | NR(1) | NR(1) | ... | U(0) |
| Data Integrity | Y(1) | ... | Y(1) | Y(1) | ... | N(0) | Y(1) | Y(1) | ... | N(0) |
| Device ID | W(1) | ... | S(2) | S(2) | ... | S(2) | S(2) | W(1) | ... | N(0) |

As shown Table 6, the user is: wearing the smart wristband for 24 hours; putting on the smart running shoes at 9:00:15; opening the application in the phone at 9:01:05 and starting walking; closing the application at 9:11:30; taking off the smart running shoes at 9:12:20 and starting walking with only the smart wristband connected to the phone; and opening the application at 9:31:25.

Correspondingly, the data synchronization in Table 6 includes the following operations.

In Minute 542, non-realtime synchronization is performed, in which the smart running shoes synchronizes data prior to the smart wristband.

Between Minute 1 and Minute 508, because the smart running shoes generate no step count, even though the smart running shoes are prioritized for synchronization, the fused physiological indicator array during this time period are replaced with the data from the smart wristband.

In Minute 541, the user puts on the smart running shoes and walks for a period of time, during which the smart running shoes generate a step count of 30 and the smart wristband generates a step count of 100. When the application in the phone is opened in Minute 542, the fused physiological indicator array is synchronized using the step count of 30 from the smart running shoes, not with the step count of 100 from the smart wristband.

When the synchronization finishes in Minute 542, because the application is still running, the application can receive changing step count data from the smart running shoes and the smart wristband, and switch to a realtime synchronization mode. In the realtime synchronization mode, the data of the smart running shoes can be synchronized to the fused physiological indicator array of the phone, and the flag array can store a value indicative of "realtime synchronization mode."

In Minute 552, the application is closed at 9:11:30. In the 30 seconds before the application is closed, the smart running shoes generate a step count of 50. In the 30 second after the application is closed, the smart running shoes generate another step count of 50. The realtime synchronization mode stops at 9:11:30 when the application is closed, and only 50 steps have been synchronized in realtime. The flag array can include values "2-0-2," indicative of "realtime synchronization," "data incomplete," and "synchronizing device being the smart running shoes," respectively.

In Minute 572, data between Minute 552 and Minute 571 can be synchronized in the non-realtime synchronization mode.

For Minute 552, because the flag array has the value "2-0-2," a difference between the element of the physiological indicator array and the corresponding element of the fused physiological indicator array can be added to the fused physiological indicator array sum, which can compensate the incomplete data of Minute 552.

In Minute 553, the smart running shoes are taken off at 9:12:20, generating a step count of 20 for the first 20 seconds of Minute 553. Because of a higher priority level, the step count of 20 is synchronized into the fused physiological indicator array and will not be replaced or changed.

In Minute 572, the synchronization is being performed at 9:31:25. In the first 25 seconds, the smart wristband generates a step count of 50, which is not stored in the wristband array and only reflected in the total step count of the smart wristband. The fused total step count can be compensated using Eq. (1), which is changed to be 5020.

According to implementations of this disclosure, when using the above-described processes, the client terminal does not need to keep data connections between each device for data synchronization, which can decrease power consumption and more effectively fuse the historical data in the physiological indicator array into the fused physiological indicator array.

The realtime synchronization can be used to display fused data with accuracy when the user is wearing smart devices and viewing the changing step count displayed on the phone in realtime as the user is walking. In other words, the realtime synchronization can be used to quickly respond to changes of the step counts of the devices, and reflect the changes in per-minute historical data.

For example, when a smart wristband of a user connects to a phone, the user can hold the phone to view the changing step count from the smart wristband, and count actual steps in heart to verify whether the step counting function of the smart wristband is accurate. In an example, the user can walk 500 steps using 3 minutes. After the 3 minutes, the user can view a page of exercise details (e.g., in an interface of the application) to view details of per-minute step counts in the 3 minutes.

In the above scenario, the per-minute step counts of the user under the realtime synchronization mode can be recorded in realtime. That is, the fused physiological indicator array can perform statistical analysis for exercise data in realtime to display the exercise details in realtime.

For another example, when the user of the smart wristband has a new pair of smart running shoes, the user can put on the smart running shoes and take off the smart wristband when the phone connects to the smart running shoes. The user can hold the phone to view the changing step count from the smart running shoes to verify whether the new shoes are correctly connected. After the user uses the smart running shoes for a period of time and takes them off, the user can put on the smart wristband again and walk, and hold the phone to view the changing step count from the smart wristband to verify whether the smart wristband is still connected.

In the above scenario, the devices switch for twice: for the first switch, the phone initially displays the step count from the smart wristband, and when the user puts on the smart running shoes, the displayed step count can accumulate in realtime as the step count from the smart running shoes changes; for the second switch, when the user takes off the smart running shoes, the displayed step count can accumulate in realtime as the step count from the smart wristband changes. The switching in this scenario is automatic, in which the user can avoid manual operations.

For the above considerations, when in the realtime synchronization mode, elements of the fused physiological indicator array can be directly manipulated to implement realtime switches between multiple devices.

For realtime single-device synchronization, the "single-device" does not mean that a user can only wear one device, but means that the realtime synchronization is performed between a single device and the phone in a period of time.

For example, a condition for the realtime synchronization can include: after performing the non-realtime synchronization, if the user leaves the application running and the total step count of the device continues to change, the total step count of the device can be broadcasted by the device and received by the phone for display in realtime.

For example, in the realtime synchronization mode, the data can be synchronized in a forward direction in time (referred to as a "chronological order"), starting from a current time.

There can be various processes to synchronize historical data from a physiological indicator array of a single device to a fused physiological indicator array in realtime. Assuming the single device having a sequence number N, the realtime synchronization can comply with some example principles described as follows.

Principle B1: "non-realtime synchronization first"

According to the principle B1, before performing the realtime synchronization, a non-realtime synchronization is performed to: synchronize all un-synchronized data to obtain a total step count of the device and a physiological indicator array sum; obtain a current fused total step count and use it as a reference value for the step counting in the realtime synchronization; determine a position in the fused physiological indicator array for data storage in the realtime synchronization; and initialize a broadcast packet table based on broadcast packets broadcasted by each device which are associated with the total step counts of the devices.

In addition, when the phone loses the connection to the device for a certain period of time, even if the application is still showing an interface for realtime display, the realtime synchronization cannot be started before performing a non-realtime synchronization.

Principle B2: "direct summing elements of fused physiological indicator array"

In the realtime synchronization, as the step count changes within a minute, the same element of the fused physiological indicator array can be repeatedly added or summed in accumulation for the minute. The reference value (e.g., used as a starting point) for the summing can be different for each minute, which is described as follows.

In a minute when the non-realtime synchronization finishes, the reference value can be determined as: reference value=(fused total step count)−(fused physiological indicator array sum).

For a new minute in a next realtime synchronization process, the reference value can be determined as: reference value=(step count included in the first broadcast packet in the new minute)−(step count included in the previous broadcast packet). The new minute can be determined according to principle B3 described as follows.

When a new broadcast packet is received, corresponding data can be changed as: for the fused physiological indicator array, after storing the reference value of the step count into the fused physiological indicator array, the corresponding element of the fused physiological indicator array can be added with a difference between a step count included in the new broadcast packet and the step count included in the previous broadcast packet; for the flag array, if the value of the corresponding element of the flag array is not "2-0-N," the value is changed to be "2-0-N" for the minute, which is indicative of "realtime synchronization," "data incomplete," and "synchronizing device having sequence number N," respectively; and for the fused total step count, it is set to be a sum of values using the fused physiological indicator array sum and the element value of the fused physiological indicator array corresponding to the minute.

Principle B3: "reconnect when time interval between connection packets is long"

When the device connects to the phone, the device can broadcast connection packets to maintain the connection. When no connection packet is received for a certain period of time, it can be determined that the device loses the connection to the phone, and the connection can be re-established to perform the non-realtime synchronization. If the connection packets are being received at regular time intervals, it can be determined that the connection between the device and the phone is normal.

Principle B4: "determine a minute ends when times of consecutive connection packets cross minutes"

For example, when the connection between the device and the phone is normal, if times of two consecutive connection packets includes a new minute (i.e., the two times cross two minutes), it can be determined that the previous minute has ended, and values of corresponding data can be changed as: for the flag array, a value "2-1-N" can be stored for the new minute, indicative of "realtime synchronization," "data complete," and "synchronizing device having sequence number N," respectively; and for the fused physiological indicator array sum, data of the new minute can be added to an element of the fused physiological indicator array corresponding to the new minute.

When the user has multiple devices, a typical scenario can be: after wearing the smart running shoes and the smart wristband for a period of time, the user opens the application in the phone to simultaneously synchronize the exercise data of both devices to the phone, and views the changing total step count in the phone as the user walks.

For example, for realtime multi-device synchronization, the following principle can be used: based on the priority levels and the principle A2, a device can be selected to be used for realtime step count display; the fused total step count can be updated by fusing the data using the selected device and not using the data from other devices; and when the selected device no longer update its step count, a new device can be selected for updating the fused total step count using the data from the selected new device.

In an implementation, a table can be used to store latest broadcast packets P(N, T, S) of each device received by the phone since the last non-realtime synchronization. Each broadcast packet of a device can include three information: a device number (N), a timestamp (T), and a total step count of the device (S). The table can also store the latest broadcast packets of a previous selected device. For example, as shown in Table 7, the priority levels of the devices are set from low to high as: smart wristband<smart watch<smart running shoes; and the device numbers are: 1 for the smart wristband, 3 for the smart watch, and 2 for the smart running shoes.

TABLE 7

| Previous Broadcast Packet | Smart Wristband Pb1 | Smart Running Shoes Ps1 | Smart Watch Pw1 | Current Selection Pw1 |
|---|---|---|---|---|
| Device Number | 1 | 2 | 3 | 3 |
| Timestamp | 17:50:31 | 17:50:20 | 17:50:33 | 17:50:33 |
| Total Step Count of Device | 2500 | 1000 | 2600 | 2600 |

Table 7 can be initialized after performing the non-realtime synchronization. The timestamps are time points when the non-realtime synchronization ends. The total step counts of the devices includes total step counts from each device. The current selected broadcast packet is null.

When a new broadcast packet is received, the new broadcast packet can be compared with a current selected broadcast packet, and it can be determined whether to switch data sources in the following three cases.

Principle B5: "summing when selected device is null or unchanged"

For example, if the previous selected device is null or the device number is unchanged, based on the principle B2, a difference between the total step count in the new broadcast packet and the total step count in the previous broadcast packet can be summed for the fused physiological indicator array, and the timestamp and the total step count of the device in the current selected broadcast packet can be updated.

For example, if a broadcast packet of the smart wristband is currently selected as Pw1=(3, 17:50:33, 2600) and the received new broadcast packet is Pw2=(3, 17:50:34, 2602), the current selected broadcast packet can be replaced with Pw2, and corresponding data can be updated as: for the fused physiological indicator array, the element can be added by 2 (2=2602−2600) in the minute; for the flag array, if the value of the element is not "2-0-3," the value can be changed as "2-0-3" indicative of "realtime synchronization," "data incomplete," and "synchronizing device having sequence number 3," respectively; and for the fused total step count, 2 can be added (2=2602−2600).

Principle B6: "switch to device with higher priority level, and conditionally sum"

For example, if the received new broadcast packet includes a priority level higher than the priority level of the current selected device, the current selected device can be switched to the device included in the received new broadcast packet. For another example, if the timestamp of the new broadcast packet and the timestamp of the current selected broadcast packet have a difference greater than or equal to a threshold value, then the difference between the total step counts of the devices in the two broadcast packets can be used for summing; otherwise, the current selected device can be changed without summing. When switching the current selected device, the current selected broadcast packet can also be switched.

In an example, a broadcast packet of the smart wristband Pw1=(3, 17:50:33, 2600) is currently selected and the threshold value for the time difference is set as 4 seconds.

If the received new broadcast packet is Ps2=(2, 17:50:34, 1010), then the current selected broadcast packet can be replaced as Ps2, the selected device can be switched to the smart running shoes, and the corresponding data can be changed as: for the fused physiological indicator array, because 17:50:34−17:50:33<4, no operation is performed; for the flag array, the value of the element can be changed to "2-0-2" indicative of "realtime synchronization," "data incomplete," and "synchronizing device having sequence number 2," respectively; and for the fused total step count, because 17:50:34-17:50:33<4, no operation is performed.

If the received new broadcast packet is Ps2=(2, 17:50:38, 1010), the current selected broadcast packet can be replaced as Ps2, the selected device can be switched to the smart running shoes, and the changing values of the step count included in the broadcast packet Ps2 can be stored in corresponding elements as: for the fused physiological indicator array, because 17:50:38−17:50:33>4, the element of the fused physiological indicator array can be added by 10 (10=1010−1000) in the minute; for the flag array, the value of the element can be changed to "2-0-2" indicative of "realtime synchronization," "data incomplete," and "synchronizing device having sequence number 2," respectively; and for the fused total step count, because 17:50:38−17:50:33>4, the fused total step count can be added by 10 (10=1010−1000) in the minute.

Principle B7: "conditionally switch to device with lower priority level, and conditionally sum"

For example, if the received new broadcast packet includes a priority level lower than the priority level of the current selected device and the timestamp of the new broadcast packet and the timestamp of the current selected broadcast packet have a difference greater than or equal to a threshold value, then: the current selected device can be switched to the device included in the received new broadcast packet; the difference between the total step counts of the devices in the two broadcast packets can be used for summing; and the current selected broadcast packet can also be switched. Otherwise, no change is made.

In an example, a broadcast packet of the smart wristband Pw1=(3, 17:50:33, 2500) is currently selected and the threshold value for the time difference is set as 4 seconds.

If the received new broadcast packet is Pb2=(1, 17:50:34, 2505), because 17:50:34 −17:50:33<4, no operation is performed.

If the received new broadcast packet is Pb2=(1, 17:50:38, 2505), because 17:50:38 −17:50:33>4, the current selected broadcast packet can be replaced as Ps2, the selected device can be switched to the smart running shoes, and the changing values of the step count included in the broadcast packet Ps2 can be stored in corresponding elements as: for the fused physiological indicator array, the element of the fused physiological indicator array can be added by 5 (5=2505−2500) in the minute; for the flag array, the value of the element can be changed to "2-0-1" indicative of "realtime synchronization," "data incomplete," and "synchronizing device having sequence number 1," respectively; and for the fused total step count, the fused total step count can be added by 5 (5=2505−2500) in the minute.

According to the principle B6, when a broadcast packet is received from a device with a higher priority level, the current selected device can be switched, and the fused total step count can be summed on a condition that the time difference between the broadcast packets exceeds the threshold; otherwise, the fused total step count is not summed. A reason for the previous operations is that, when two devices are generating data at the same time, the data of the two devices represent the same walking status during the same time period. The fused total step count would be greater than expected if it is summed without the condition. When the time difference is greater than the threshold, it can be determined that there is only one device counting the steps, and other devices are not used for counting during the time period. The fused total step count would be more accurate if summed under the condition.

Table 8 shows an example scenario in a minute. In the minute, the user performs non-realtime synchronization for a smart wristband and smart running shoes; walks wearing the smart wristband then puts on the smart running shoes; and takes off the smart wristband and walks for a period of time wearing the smart running shoes. In some cases, when the first broadcast packet after generation of a step count by the smart running shoes and the last broadcast packet of the smart wristband have a very short time difference, the fused step count can be smaller than expected with an insignificant amount.

The third and fourth line shows the step counts and times broadcasted by the smart wristband.

The fifth and sixth line shows the step counts and times broadcasted by the smart running shoes.

The seventh line shows the selected broadcast device after the phone receives broadcast packets from the two devices.

The eighth line shows the fused total step count determined by the phone after performing realtime synchronization based on the selected broadcast device.

In some implementations, for example, an internal logic of a step counting device can be set as that the device will not send the first broadcast packet until its total step count reaches 10. For example, the internal logic can be used to filter inaccurate step counts, in which the step count of the device would not be determined as valid until it reaches a predetermined threshold. If the step count of the device is determined as invalid, it can be reset to restart the counting.

In this example scenario, it is set that the first broadcast packet would not be sent until the total step count reaches 10. After the first broadcast packet is sent, following broadcast packets will be sent as long as the step count changes.

As shown in Table 8, before the step count of the smart running shoes are broadcasted, there is a time overlap (Seconds 14-17) for step counting between the smart wristband and the smart running shoes. After the total step count of the smart running shoes reaches 10, the first broadcast packet of the smart running shoes is sent in Second 20, which differs from the time of broadcast packet of the previously selected smart wristband (Second 17) by 3 seconds, less than the set threshold 4 seconds. Based on the principle B6, the current selected device can be switched from the smart wristband to the smart running shoes. The step count of the smart running shoes will not be added to the fused total step count in the data synchronization.

As shown in Table 8 for this example scenario, between Seconds 17-20, the step count of the smart running shoes is

TABLE 8

| Time (s) | | 5 | 10 | | 15 | 17 | 20 | | 25 | |
|---|---|---|---|---|---|---|---|---|---|---|
| Event | | NR | Walk with Wristband | | | Walk with Shoes | Wristband Off | | | |
| Wristband Broadcast | Steps | 100 | | | 110 | 113 | 116 | 120 | | |
| | Time | | | | | | | | | |
| Shoes Broadcast | Steps | 0 | | | | | 10 | 13 | 16 | 20 |
| | Time | | | | | Lost | | | | |
| Selected Broadcast | | | | W | W | W | W | S | S | S | S |
| Fused Total Steps | | 100 | | | 110 | 113 | 116 | 120 | 120 | 123 | 126 | 130 |

In this example scenario as shown in Table 8, each line is described as follows.

The first line shows time in unit of seconds.

The second line shows user events: the user performs non-realtime synchronization in Second 5; the user walks wearing the smart wristband in Second 7; 4 broadcast packets are received from the smart wristband in Seconds 12, 14, 16, and 17; the user takes the smart wristband off at Second 18; the user puts on the smart running shoes and walks at Second 14; and 4 broadcast packets are received from the smart running shoes in Seconds 20, 21, 24, and 26.

not synchronized, and not summed in the fused total step count, which might cause the fused total step count smaller than expected with an insignificant amount.

Similarly, in some cases, data synchronization based on the principles B6 and B7 can cause the fused total step count greater than expected with an insignificant amount.

Table 9 shows another example scenario similar to Table 8 with a slight difference: the time when the smart running shoes broadcast their first broadcast packet after generating step count is Second 22.

TABLE 9

| Time (s) | | 5 | 10 | | 15 | 17 | 20 | | 25 | | |
|---|---|---|---|---|---|---|---|---|---|---|---|
| Event | | NR | Walk with Wristband | | Walk with Shoes | | Wristband Off | | | | |
| Wristband Broadcast | Steps | 100 | | 110 | 113 | 116 | 120 | | | | |
| | Time | | | | | | | | | | |
| Shoes Broadcast | Steps | 0 | | | | | | | 10 | 12 | 14 |
| | Time | | | | Extra | | | | | | |
| Selected Broadcast | | | W | W | W | W | | | S | S | S |
| Fused Total Steps | | 100 | | 110 | 113 | 116 | 120 | | 130 | 132 | 134 |

As shown in Table 9, before the step count of the smart running shoes are broadcasted, there is a time overlap (Seconds 14-17) for step counting between the smart wristband and the smart running shoes. After the total step count of the smart running shoes reaches 10, the first broadcast packet of the smart running shoes is transmitted in Second 22, which differs from the time of broadcast packet of the previously selected smart wristband (Second 17) by 5 seconds, greater than the set threshold 4 seconds. Based on the principle B6, the current selected device can be switched from the smart wristband to the smart running shoes, and the step count of the smart running shoes will be added to the fused total step count in the data synchronization.

As shown in Table 9 for this example scenario, between Seconds 14-17, the step count of the smart running shoes is summed into the fused total step count, which might cause the fused total step count greater than expected with an insignificant amount.

Tables 8-9 shows two example scenarios in which the fused total step count is smaller or greater than expected. However, similar scenarios only happen when the current selected device is switched, and affected step count is limited within a few second with an insignificant amount.

In an example, when a client terminal of a user performs data synchronization in a realtime synchronization mode, corresponding data can be shown in Table 10.

TABLE 10

| Time (s) | | 50 | 55 | | | 0 | | 5 | | 10 |
|---|---|---|---|---|---|---|---|---|---|---|
| Event | | NR | Walk with Band | Walk with Shoes | | | Shoes Off | | | |
| Wristband Broadcast | Steps | 100 | | 110 | 115 | 120 | 125 | 130 | 135 | 140 | 145 | 150 |
| | Time | | | | | | | | Lost | | | |
| Shoes Broadcast | Steps | 0 | | | 10 | 16 | 22 | 28 | | | |
| | Time | | | Lost | | | | | | | |
| Selected Broadcast | | | W | W | S | S | S | S | W | W | W |
| Fused Total Steps | | 100 | 110 | 115 | 115 | 121 | 127 | 133 | 138 | 143 | 148 |
| Fusion Array | | 0 | 110 | 115 | 115 | 121 | 6 | 12 | 17 | 22 | 27 |
| Flag Array | | 0-0-0 | 2-0-1 | 2-0-1 | 2-0-2 | 2-1-2 | 2-0-2 | 2-0-2 | 2-0-1 | 2-0-1 | 2-0-1 |

As shown in Table 10, in this example, the user: wears the smart wristband in the whole process; puts on the smart running shoes and walks for a while; and takes off the smart running shoes. In this example, the selected device for realtime synchronization is the smart wristband at the beginning, and switches to the smart running shoes when the smart running shoes are put on. In Second 50, non-realtime synchronization is performed. After that, the step count of the smart wristband is synchronized for 9 times in: Second 54 for 110 steps; Second 56 for 115 steps; Second 58 for 120 steps; Second 0 for 125 steps; Second 2 for 130 steps; Second 5 for 135 steps; Second 7 for 140 steps; Second 8 for 145 steps; and Second 11 for 150 steps. The step count of the smart running shoes is synchronized for 4 times in: Second 57 for 10 steps; Second 59 for 16 steps; Second 1 for 22 steps; and Second 3 for 28 steps.

The data synchronization can include the following operations.

In Second 50, the non-realtime synchronization is performed. Because it is uncertain that whether the user will move, the fused physiological indicator array and the flag array can be unchanged.

In Second 54, the step count of the smart wristband changes, and it can be determined that the realtime synchronization mode is started. A difference between the first step count of the first synchronization in the new minute and the step count of the last synchronization is added to the fused total step count. A difference between the fused total step count and the fused physiological indicator array sum is stored to an element of the fused physiological indicator array corresponding to the new minute. The element of the flag array stores a value "2-0-1" indicative of "realtime synchronization," "data incomplete," and "last selected device being the smart wristband," respectively.

In Second 57, the step count of the smart running shoes changes. Because the priority level of the smart running shoes is higher than the smart wristband, the selected device for synchronization is switched to the smart running shoes. Because the time difference (3 seconds) between the current data synchronization and the last data synchronization is smaller than a predetermined threshold (4 seconds), no compensation data is stored, but the element of the flag array is changed to "2-0-2" indicative of "realtime synchronization," "data incomplete," and "last selected device being the smart running shoes," respectively.

In Second 0, because the new minute starts ("crossing minutes"), the element of the flag array is changed to "2-1-2" indicative of"realtime synchronization," "data complete," and "last selected device being the smart running shoes," respectively.

In Second 1, and the element of the flag array is changed to "2-0-2" for the new minute, indicative of "realtime synchronization," "data incomplete," and "last selected device being the smart running shoes," respectively.

In Second 3, the step count of the smart running shoes continues to be synchronized, and then the smart running shoes disconnects to the phone.

In Second 7, the phone connects to the smart wristband, and starts to synchronize the step count of the smart wristband. Because the time interval since the smart running shoes disconnecting to the phone reaches the predetermined threshold (4 seconds), a difference (5 steps) between the step count of the smart wristband in the current broadcast packet (140 steps) and the step count of the smart wristband in the previous broadcast packet (135 steps) is added for the fused physiological indicator array. The element of the flag array stores a value "2-0-1" indicative of "realtime synchronization," "data incomplete," and "last selected device being the smart wristband," respectively.

In Second 8, the step count of the smart wristband continues to be synchronized and added to the fused physiological indicator array.

As shown in the above-described implementations, the user can view the changes of the step count in a client terminal in realtime. The client terminal can provide realtime data synchronization and non-realtime data synchronization for the user to select according to various scenarios, which can improve data statistics.

Figure 4:
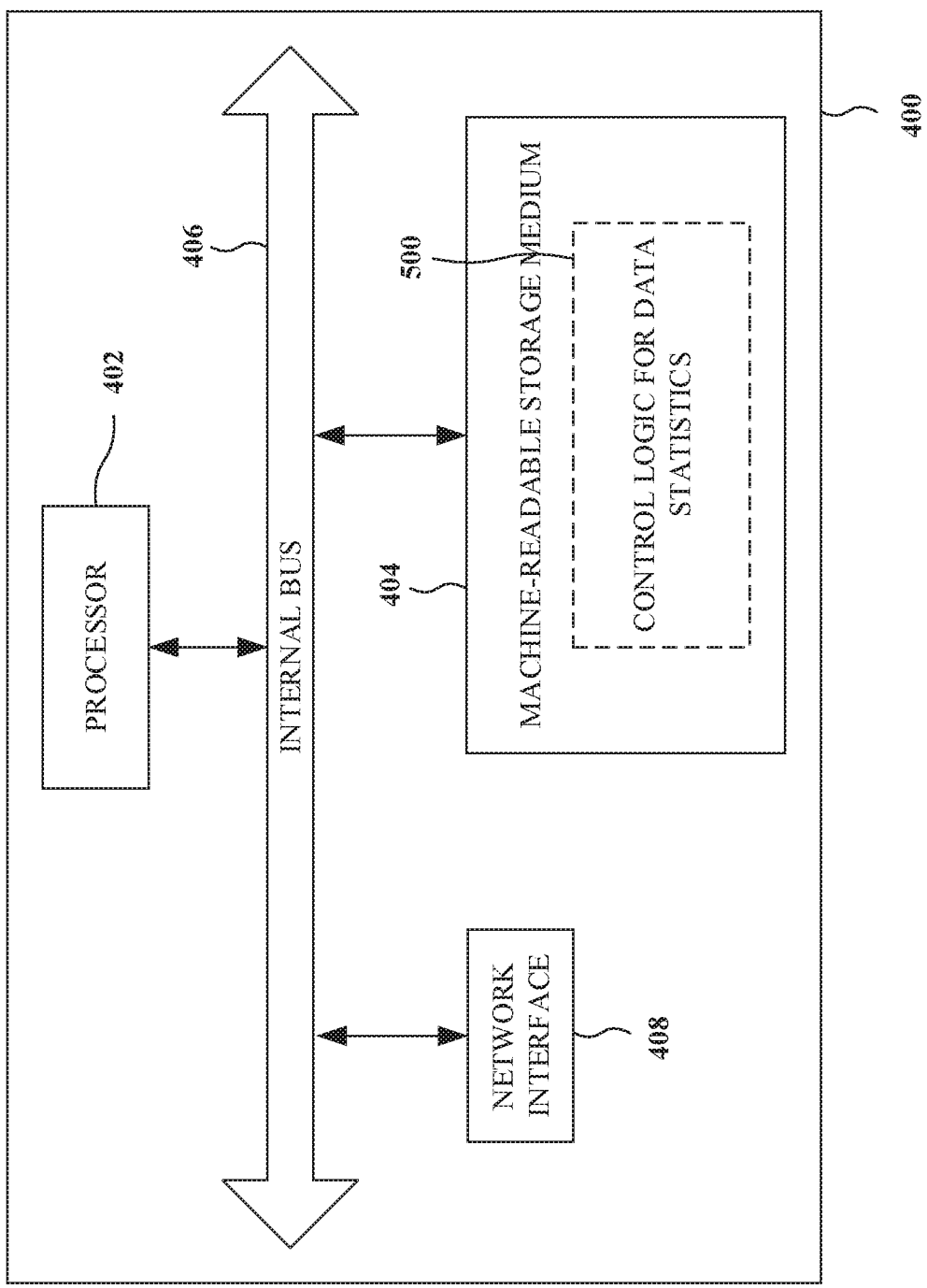
FIG. 4 is a diagram of an example apparatus for data statistics according to an implementation of this disclosure.

As shown in FIG. 4, according to implementations of this disclosure, an example apparatus 400 for data statistics is provided. The apparatus can include a smart wearable device. The apparatus 400 shown in FIG. 4 includes a processor 402 and a machine-readable storage medium 404. The processor 402 and the machine-readable storage medium 404 are interconnected by an internal bus 406. In other implementations, in addition, the apparatus 400 can also include an external network interface 408 for communication with other devices or components.

The machine-readable storage medium 404 can include a non-transitory storage medium, a flash drive, a hard drive, a solid state drive, an optical/magnetic disc (e.g., a CD or a DVD), or any combination of any suitable type of storage device.

Figure 5:
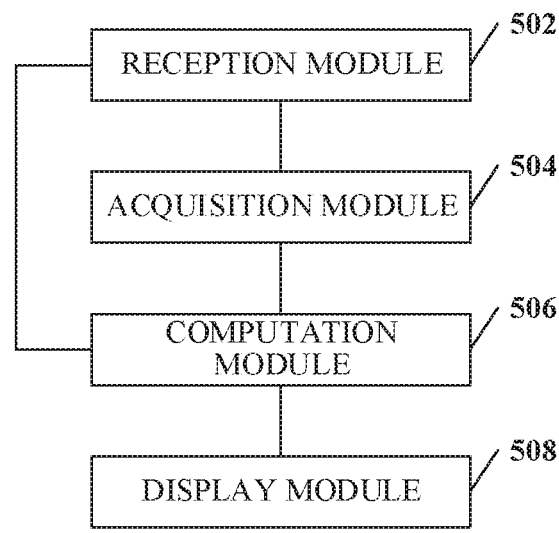
FIG. 5 is a diagram of an example control logic for data statistics according to an implementation of this disclosure.

The machine-readable storage medium 404 can store machine-executable instructions corresponding to a control logic 500 for controlling data statistics for wearable devices. As shown in FIG. 5, grouped by function, the control logic 500 can include the following modules. The modules of the control logic 500 can be implemented as hardware or software. For example, the hardware implementation can be one or more special- or general-purpose chips or integrated circuits (e.g., a processor, a memory, or a non-transitory storage medium) for performing the operations included in the control logic. For another example, the software implementation can include program codes or instructions which when executed by a processor become operational with the processor to execute the operations included in the control logic.

A reception module 502 can be configured to, when receiving physiological indicator data for a statistical item of a user using multiple smart devices, receive the physiological indicator data time information associated with the physiological indicator data collected by at least one smart device of the multiple smart devices.

An acquisition module 504 can be configured to acquire a priority level for each smart device.

A computation module 506 can be configured to compute fused physiological indicator data for the statistical item of the user based on the priority level of each smart device, the physiological indicator data, and the time information associated with the physiological indicator data.

A display module 508 can be configured to display the fused physiological indicator data.

In an implementation, the physiological indicator data can include at least one of: a step count, a movement distance, a heartbeat count, and an energy consumption value.

In an implementation, the physiological indicator data can be stored in an array with a predetermined size (e.g., a physiological indicator array). Each smart device can correspond to an array. Physiological indicator data received by each device at a temporal granularity can be stored as an element of the array. In other words, when receiving the physiological indicator data at the temporal granularity, the element can be associated with a timestamp. In the implementation, for example, the computation module 506 can be used to determine respective fused physiological indicator data in a fused physiological indicator array based on the priority level device and a corresponding physiological indicator array of each smart.

Figure 6:
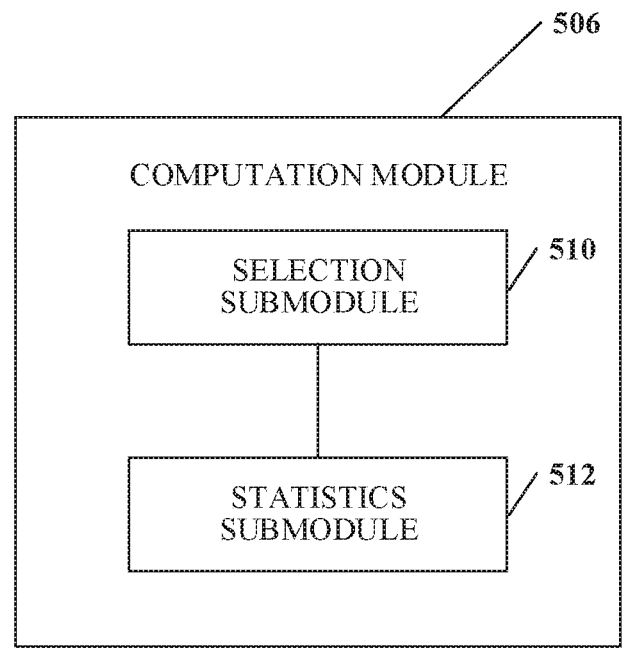
FIG. 6 is a diagram of an example calculation module in a control logic for data statistics according to an implementation of this disclosure.

As shown in FIG. 6, in an implementation, the computation module 506 can include the following submodules.

A selection submodule 510 can be configured to select a target smart device as a smart device having the highest priority level and meeting a time requirement based on the priority level and the time information associated with the physiological indicator data of each smart device.

A statistics submodule 512 can be configured to analyze statistics of physiological indicator data of the target smart device to obtain a statistical result, and determine the statistical result as the fused physiological indicator data.

In an implementation, the statistics submodule 512 can be further configured to, when the physiological indicator data of the target smart device is incomplete or null, select a new target smart device as a smart device having the next highest priority level and meeting the time requirement, and replace the physiological indicator data of the target smart device with physiological indicator data of the new target smart device.

In an implementation, the statistics submodule 512 can be further configured to: determine whether a data synchronization mode for the multiple smart devices is a non-realtime synchronization mode or a realtime synchronization mode; when the data synchronization mode is the non-realtime synchronization mode, determine corresponding fused physiological indicator data by analyzing the statistics of the physiological indicator data of the target smart device from a first un-synchronized time to a current time; and when the data synchronization mode is the realtime synchronization mode, determine the corresponding fused physiological indicator data by analyzing statistics of current physiological indicator data of the target smart device.

In an implementation, the statistics submodule 512 can be further configured to: when the target smart device is detected to change from a first smart device to a second smart device, receive historical physiological indicator data of the first smart device and current physiological indicator data of the second smart device; and determine the fused physiological indicator data based on the historical physiological indicator data of the first smart device and the current physiological indicator data of the second smart device.

In an implementation, the statistics submodule 512 can be further configured to: determine a time difference between the current time and a historical time associated with the historical physiological indicator data of the first smart device; when the time difference is greater than or equal to a predetermined threshold value, determine the fused physiological indicator data by summing the historical physiological indicator data of the first smart device, the current physiological indicator data of the second smart device, and predetermined physiological indicator data for compensation; and when the time difference is smaller than the predetermined threshold value, determine the fused physiological indicator data by summing the historical physiological indicator data of the first smart device and the current physiological indicator data of the second smart device.

It should be understood that implementations of this disclosure can be provided as a method, a system, or a computer program product. Thus, this disclosure can be implemented as software, hardware, or a combination thereof. Moreover, this disclosure can be implemented as a computer-readable storage medium including computer-usable program codes. The computer-readable storage medium can include a disk storage, an optical memory, or similar devices, on which a computer program product is implemented.

This disclosure has been described with reference to flowcharts and/or block diagrams of processes, apparatuses, systems, and computer program products according to implementations of this disclosure. It should be understood that each process and/or box and a combination of processes and boxes in the flowcharts and/or block diagrams can be implemented by computer program instructions. The computer program instructions can be provided to a processor of a general-purpose computer, a special-purpose computer, an embedded processor, or a programmable data processing device to form a machine. Instructions executed by a processor of a computer or other programmable data processing devices can implement a device for the functions specified in one or more processes of the flowcharts and/or one or more boxes of the box diagrams.

The computer program instructions can also be stored in a computer-readable storage capable of operating a computer or another programmable data processing device in a particular manner. Instructions stored in the computer readable storage can produce a product that includes a device, in which the device can implement a function specified in one or more processes in the flowcharts and/or one or more boxes in the block diagrams.

For implementations of the apparatuses, because they substantially correspond to the implementations of the methods, details of them can be referred to the description of the implementations of the methods. The implementations of the apparatuses described above is merely illustrative, in which the units described as separating parts can or cannot be physically separate. The parts shown as units can or cannot be physical units; that is, the parts can be at one place, or distributed as multiple elements over a network. Part or all of the modules can be selected according to actual needs to achieve the object of this disclosure. One ordinary skilled in the art can understand and practice implementations of this disclosure and their variations without creative work.

It should be noted that, in this disclosure, relational terms such as "first" and "second" are only used to distinguish an entity or an operation from another entity or another operation without necessarily requiring or implying that the entities or operations have any such relationship or sequence. The terms "comprise," "include," or any other variant thereof are intended to encompass a non-exclusive inclusion, such that the processes, methods, products or apparatuses comprising a series of elements include not only those elements but also other elements not explicitly listed, or elements inherent to the processes, methods, products or apparatuses. Without more restrictions, an element limited by a statement "including . . . " does not preclude the presence of additional elements in the processes, methods, products or apparatuses that includes the element.

The methods and apparatus provided in the implementations of this disclosure have been described in detail. The principles and implementations of this disclosure have been described with reference to examples. The description of the above implementations is merely for explaining the methods and principles of this disclosure. In addition, it should be understood that, according to the teachings of this disclosure, changes are permitted in the scope and implementations of this disclosure. This specification is not to be construed to limit the scope of this disclosure.

What is claimed is:

1. A method of using a client terminal of a user for integrating data from multiple wearable devices worn by the user, the method comprising:
   collecting, at the client terminal, unsynchronized physiological indicator data and a timestamp representative of a time at which the unsynchronized physiological indicator data was recorded from each wearable device of the multiple wearable devices, wherein each unsynchronized physiological indicator data represents a statistical item for the user, and wherein at least one of the timestamps is collected from a wearable device having a clock cycle which differs from a clock cycle of the client terminal;
   determining, at the client terminal, fused physiological indicator data representing a shared measurement of the statistical item among each wearable device of the multiple wearable devices by:
      identifying a synchronization mode to use to synchronize the unsynchronized physiological indicator data; and
      determining, based on the synchronization mode, the fused physiological indicator data by synchronizing, into a synchronized data storage format, the unsynchronized physiological indicator data according to the timestamps,
      wherein when the synchronization mode is a non-realtime synchronization mode, determining the fused physiological indicator data includes using a reverse chronological order for the unsynchronized physiological indicator data collected between a current timestamp and an earlier timestamp for which no synchronization has been performed, and
      wherein when the synchronization mode is a realtime synchronization mode, determining the fused physiological indicator data includes using a chronological order for the unsynchronized physiological indicator data; and
   outputting, at the client terminal, the fused physiological indicator data to a display of the client terminal to visually represent the synchronization of the unsynchronized physiological indicator data collected from the multiple wearable devices.

2. The method of claim 1, wherein
   each of the multiple wearable devices is associated with a physiological indicator array having a predetermined size, and the unsynchronizeed physiological indicator data, at a time interval, comprises data associated with the time interval in the physiological indicator array; and
   the fused physiological indicator data is associated with a fused physiological indicator array having the predetermined size, and the fused physiological indicator data, at the time interval, is stored in a corresponding element of the fused physiological indicator array.

3. The method of claim 2, wherein determining the fused physiological indicator by synchronizing the unsynchronized physiological indicator data according to the timestamps comprises:
   determining the fused physiological indicator data based on, for each of the multiple wearable devices, a priority level and the physiological indicator array.

4. The method of claim 1, wherein the unsynchronized physiological indicator data includes first physiological indicator data collected from a first wearable device of the multiple wearable devices and second physiological indicator data collected from a second wearable device of the multiple wearable devices, and
   wherein determining the fused physiological indicator data by synchronizing the unsynchronized physiological indicator data according to the timestamps comprises:
   determine the fused physiological indicator data based on a priority level associated with the first wearable device, a priority level associated with the second wearable device, the first physiological indicator data, the second physiological indicator data, the timestamp associated with the first physiological indicator data, and the timestamp associated with the second physiological indicator data.

5. The method of claim 1, wherein determining the fused physiological indicator data by synchronizing the unsynchronized physiological indicator data according to the timestamps comprises:
   selecting a target wearable device from the multiple wearable devices based on a priority level and a timestamp associated with the unsynchronized physiological indicator data collected from the target wearable device,
   wherein the target wearable device is selected from the multiple wearable devices based on a highest priority level of the multiple wearable devices, when a difference between the timestamp associated with the target wearable device and the timestamp associated with another wearable device does not exceed a threshold.

6. The method of claim 5, further comprising:
   when the data is being integrated from the multiple wearable devices in the realtime synchronization mode, prior to determining the fused physiological indicator data using the unsynchronized physiological indicator data collected by the target wearable device, determining the fused physiological indicator data using the unsynchronized physiological indicator data collected by the target wearable device between the current timestamp and an earlier timestamp for which no synchronization has been performed.

7. The method of claim 5, wherein determining the fused physiological indicator data by synchronizing the unsynchronized physiological indicator data according to the timestamps comprises:
   when the target wearable device is detected to change from a first wearable device to a second wearable device, receiving historical physiological indicator data from the first wearable device and current physiological indicator data from the second wearable device; and
   determining the fused physiological indicator data based on the historical physiological indicator data from the first wearable device and the current physiological indicator data from the second wearable device.

8. The method of claim 7, wherein determining the fused physiological indicator data based on the historical physiological indicator data from the first wearable device and the current physiological indicator data from the second wearable device comprises:
   determining a difference between the current timestamp and a historical timestamp associated with the historical physiological indicator data from the first wearable device;
   based on a determination that the difference is greater than or equal to a threshold, determining the fused physiological indicator data by summing the historical physiological indicator data from the first wearable device, the current physiological indicator data from the second wearable device, and predetermined physiological indicator compensation data; and based on a determination that the difference is smaller than the threshold, determining the fused physiological indicator data by summing the historical physiological indicator data from the first wearable device and the current physiological indicator data from the second wearable device.

9. The method of claim 7, further comprising:
based on a determination that a priority level of the second wearable device is higher than a priority level of the first wearable device, determining the target wearable device as the second wearable device; and based on a determination that the priority level of the second wearable device is lower than the priority level of the first wearable device and a difference between the current timestamp and a historical timestamp associated with the historical physiological indicator data is greater than or equal to a threshold, determining the target wearable device as the second wearable device.

10. The method of claim 1, wherein the unsynchronized physiological indicator data comprises at least one of a step count, a movement distance, a heartbeat count, and an energy consumption value.

11. The method of claim 1, wherein a priority level for each of the multiple wearable devices is determined based on at least one of an accuracy of the physiological indicator data collected by the wearable device, and a predetermined priority level for the wearable device.

12. A client terminal apparatus for integrating data from multiple wearable devices worn by a user of the client terminal apparatus, the client terminal apparatus comprising:
a display;
a processor; and
a memory configured to store instructions which when executed by the processor become operational with the processor to:
collect, from each wearable device of the multiple wearable devices, unsynchronized physiological indicator data and a timestamp at which the unsynchronized physiological indicator data was recorded, wherein each unsynchronized physiological indicator data represents a statistical item for the user, and;
determine fused physiological indicator data representing a shared measurement of the statistical item among each wearable device of the multiple wearable devices by:
identifying a synchronization mode to use to synchronize the unsynchronized physiological indicator data; and
determining, based on the synchronization mode, the fused physiological indicator data the fused physiological indicator data by synchronizing, into a synchronized data storage format, the unsynchronized physiological indicator data according to the timestamps; and
output the fused physiological indicator data to the display to visually represent the synchronization of the unsynchronized physiological indicator data collected from the multiple wearable devices.

13. The client terminal apparatus of claim 12, wherein the instructions operational with the processor to collect the unsynchronized physiological indicator data and the timestamp associated at which the unsynchronized physiological indicator data was recorded further comprise instructions to:
receive, from a first wearable device of the multiple wearable devices, first physiological indicator data associated with the statistical item being collected for the user and a timestamp associated with the first physiological indicator data; and receive, from a second wearable device of the multiple wearable devices, second physiological indicator data associated with the statistical item being collected for the user and a timestamp associated with the second physiological indicator, and wherein the instructions operational with the processor to determine the fused physiological indicator data by synchronizing the unsynchronized physiological indicator data according to the timestamps further comprise instructions to:
determine the fused physiological indicator data based on a priority level associated with the first wearable device, a priority level associated with the second wearable device, the first physiological indicator data, the second physiological indicator data, the timestamp associated with the first physiological indicator data, and the timestamp associated with the second physiological indicator data.

14. The client terminal apparatus of claim 12, wherein the instructions operational with the processor to determine the fused physiological indicator data by synchronizing the unsynchronized physiological indicator data according to the timestamps further comprise instructions to:
when historical physiological indicator data comprises incomplete or null data at a time interval between a current timestamp and an earlier timestamp, select a target wearable device from the multiple wearable devices based on a highest priority level among the multiple wearable devices; and
determine the fused physiological indicator data at the time interval using the unsynchronized physiological indicator data collected by the target wearable device at the time interval.

15. The client terminal apparatus of claim 12, wherein the memory further comprises instructions when executed by the processor become operational with the processor to:
select a target wearable device from the multiple wearable devices based on a highest priority level among the multiple wearable devices;
when the synchronization mode is realtime synchronization mode, receive, from the target wearable device, current physiological indicator data collected by the target wearable device and a current timestamp associated with the current physiological indicator data;
determine the fused physiological indicator data in a reverse chronological order using historical physiological indicator data; and
determine the fused physiological indicator data in a chronological order based on the current pphysiological indicator data.

16. The client terminal apparatus of claim 15, wherein the instructions operational with the processor to determine the fused physiological indicator data in the chronological order based on the current physiological indicator data further comprise instructions to:
receive, from an additional wearable device, additional physiological indicator data collected by the additional wearable device and an additional timestamp associated with the additional physiological indicator data;
based on a determination that a priority level of the additional wearable device is higher than a priority level of the target wearable device, determine the target wearable device as the additional wearable device; and based on a determination that a difference between the additional timestamp and the current timestamp is greater than or equal to a threshold, determine the fused physiological indicator data by summing a difference between the additional physiological indicator data and earlier physiological data collected by the additional wearable device.

17. The client terminal apparatus of claim 16, wherein the memory further comprises instructions when executed by the processor become operational with the processor to:
based on a determination that the priority level of the additional wearable device is lower than the priority level of the target wearable device and a difference between the additional timestamp and the current timestamp is greater than or equal to a threshold, determine the target wearable device as the additional wearable device; and
determine the fused physiological indicator data by summing a difference between the additional physiological indicator data and earlier physiological data collected by the additional wearable device.

\* \* \* \* \*